US009603881B2

(12) United States Patent
Koganov et al.

(10) Patent No.: US 9,603,881 B2
(45) Date of Patent: Mar. 28, 2017

(54) BIOACTIVE FRACTIONS FROM STRESS-INDUCED PHOTOSYNTHETIC ORGANISMS AND METHODS OF THEIR MANUFACTURE AND USE

(75) Inventors: Michael Koganov, White Plains, NY (US); Olga Dueva-Koganov, White Plains, NY (US); Paul Recht, Briarcliff Manor, NY (US); Artyom Duev, White Plains, NY (US)

(73) Assignee: ISP INVESTMENTS LLC, Wilmington, DE (US)

( * ) Notice: Subject to any disclaimer, the term of this patent is extended or adjusted under 35 U.S.C. 154(b) by 23 days.

(21) Appl. No.: 12/945,323

(22) Filed: Nov. 12, 2010

(65) Prior Publication Data
US 2011/0110872 A1  May 12, 2011

Related U.S. Application Data

(60) Provisional application No. 61/260,095, filed on Nov. 11, 2009.

(51) Int. Cl.
| | |
|---|---|
| *A61K 36/02* | (2006.01) |
| *A61K 36/03* | (2006.01) |
| *A61K 36/05* | (2006.01) |
| *A61K 8/97* | (2017.01) |
| *A61Q 19/00* | (2006.01) |
| *A61Q 19/08* | (2006.01) |
| *C12N 1/12* | (2006.01) |

(52) U.S. Cl.
CPC .............. *A61K 36/02* (2013.01); *A61K 8/975* (2013.01); *A61Q 19/00* (2013.01); *A61Q 19/08* (2013.01); *C12N 1/12* (2013.01)

(58) Field of Classification Search
CPC .......... A61K 36/02; A61K 36/03; A61K 36/05
See application file for complete search history.

(56) References Cited

U.S. PATENT DOCUMENTS

| | | | | |
|---|---|---|---|---|
| 7,208,160 B2* | 4/2007 | Katzen | ................... | A61K 36/02 424/195.17 |
| 8,697,427 B2* | 4/2014 | Franklin | .................. | C12N 9/00 435/134 |

(Continued)

FOREIGN PATENT DOCUMENTS

| | | | |
|---|---|---|---|
| JP | 05-068585 | | 3/1993 |
| JP | 57036859 | * | 9/2014 |

(Continued)

OTHER PUBLICATIONS

H.B. MacPhillamy: Drugs From Plants; Plant Science Bulletin, Botanical Society of America, vol. 9, No. 2, Apr. 1963.*

(Continued)

*Primary Examiner* — Chris R Tate
(74) *Attorney, Agent, or Firm* — FisherBroyles, LLP; William J. Davis

(57) ABSTRACT

The present invention relates to bioactive fractions isolated from stress-induced photosynthetic organisms. The present invention also relates to methods of producing stress-induced photosynthetic organisms suitable for isolating altered bioactive fractions. The present invention further relates to bioactive compositions, bioactive topical formulations, and methods of their use.

14 Claims, 10 Drawing Sheets

(56) References Cited

U.S. PATENT DOCUMENTS

| | | | |
|---|---|---|---|
| 2005/0048080 A1* | 3/2005 | Katzen | A61K 36/02 424/195.17 |
| 2005/0142219 A1* | 6/2005 | Dunuwila | A61K 33/00 424/722 |
| 2007/0196523 A1 | 8/2007 | Koganov | |
| 2007/0224216 A1* | 9/2007 | Teas | A61K 35/748 424/195.17 |
| 2009/0098637 A1 | 4/2009 | Muir et al. | |
| 2009/0130139 A1 | 5/2009 | Mekideche | |
| 2009/0185990 A1 | 7/2009 | Koganov | |
| 2011/0045528 A1* | 2/2011 | Dhamwichukorn | C12N 1/06 435/41 |
| 2011/0151507 A1* | 6/2011 | van Walsem | C12M 21/02 435/41 |
| 2011/0152144 A1* | 6/2011 | Copp | C10L 5/361 508/216 |
| 2012/0189706 A1* | 7/2012 | Copp | C10L 5/361 424/522 |

FOREIGN PATENT DOCUMENTS

| | | | |
|---|---|---|---|
| WO | 03/063803 A1 | 8/2003 | |
| WO | 2007/110511 A1 | 10/2007 | |

OTHER PUBLICATIONS

Houvinen et al. Impact of UV Radiation on the Early Development of the Giant Kelp (Macrocystis Pyrifera) Gametophytes; Phytochemistry and Photobiology, 2000, 72(3): 308-313.*

Phillipson, J. New Drugs From Nature—It Could Be Yew; Phytotherapy Research 13 (1999) pp. 2-8.*

Raskin et al. Can an Apple a Day Keep the Doctor Away? Current Pharmaceutical Design, 2004, 10, 3419-3429.*

Revilla et al. Comparison of Several Procedures Used for the Extraction of Anthocynains From Red Grapes; J. Agric. Food Chem. 1998, 46, pp. 4592-4597.*

International Search Report and Written Opinion issued in PCT/US2010/056520, mailed Jul. 29, 2011.

Townsend, Brigitte E., "Identification of Marine Antioxidants," Paper for Master of Science Degree, The University of Georgia (2008).

Extended European Search Report issued in European Patent Application No. 10830782.8, mailed May 7, 2013.

Koivikko et al., "Contents of soluble, cell-wall-bound and exuded phlorotannins in the brown alga *Fucus vesiculosus*, with implications on their ecological functions," *J. Chemical Ecology*, 31(1):1573-1561 (2005).

Hammerstrom et al., "Rapid Phlorotannin Induction and Relaxation in Five Washington Kelps," *Marine Ecology Progress Series*, 165:293-305 (1998).

Heo et al., "Effect of phlorotannins isolated from *Ecklonia cava* on melanogenesis and their protective effect against photo-oxidative stress induced by UV-B radiation," *Toxicology* in Vitro, 23(6):1123-1130 (2009).

Swanson et al., "Induction, Exudation and the UV Protective Role of Kelp Phlorotannins," *Aquatic Botany*, 73(3):241-253 (2002).

Agrawal, S.B., "Effects of Supplemental U.V.-B Radiation on Photosynthetic Pigment, Protein and Glutathione Contents in Green Algae," *Environmental and Experimental Botany*, 32(2):137-143 (1992).

* cited by examiner

BIOACTIVE FRACTIONS FROM STRESS-INDUCED PHOTOSYNTHETIC ORGANISMS AND METHODS OF THEIR MANUFACTURE AND USE

CROSS-REFERENCE TO RELATED APPLICATIONS

This application claims the benefit of U.S. Provisional Patent Application Ser. No. 61/260,095, filed Nov. 11, 2009, which is hereby incorporated by reference in its entirety.

FIELD OF THE INVENTION

The present invention relates to bioactive fractions isolated from stress-induced photosynthetic organisms, methods of isolating the bioactive fractions, methods of using the bioactive fractions, and compositions and formulations containing the bioactive fractions.

BACKGROUND OF THE INVENTION

Environmental stresses are major limiting factors of plant development, growth and productivity. There are two general types of stress factors that can produce plant responses: (1) abiotic, which arise from excesses or deficiencies in the environment, and (2) biotic, which are imposed by other organisms.

Plant responses to stress factors trigger modulation of cellular metabolism, altered gene expression, changes in the growth rate, yield of phytomass, and reproductive capabilities. The following conditions, among others, cause plant stress: water-logging and submergence, drought, high or low temperatures, high or low soil salinity, inadequate minerals in the soil, too much or too little light, exposure to high concentrations of ozone and underexposure or overexposure to UV light.

Resistance or sensitivity of photosynthetic organisms to the stress depends on the species, genotype and development age. There are three major stress resistance mechanisms: (1) avoidance mechanisms which prevent exposure to the stress; (2) tolerance mechanisms which permit the plant to withstand stress; and (3) acclimation, i.e., alteration of plant physiology in response to stress.

Stress response is initiated when plants recognize stress at the cellular level and then stress recognition activates signal transduction pathways that transmit information within the individual cell and throughout the plant. Regulators of plant stress response include, but are not limited to, abscisic and jasmonic acids, osmotic adjustment factors, osmotin, protein stabilizing factors, heat shock proteins, specific mRNAs, $Ca^{2+}$ ions and defense-related secondary metabolites.

The impressive ability of plants to sustain high levels of multiple stresses indicates that the defense mechanism is very complex in nature and involves multiple mechanisms of cellular adaptation and numerous metabolic pathways. Although this comprehensive and powerful defense system is not completely understood yet, utilization of its components and their interactions can be very beneficial.

U.S. Patent Application Publication No. 2009/0031446 discloses stress-related polypeptides and methods of use in plants: a transgenic plant transformed with an SLSRP coding nucleic acid, wherein expression of the nucleic acid sequence in the plant results in increased growth under water-limited conditions and/or increased tolerance to an environmental stress as compared to a wild type variety of the plant.

It was shown that synthesis of rutin, an antioxidative flavonoid in buckwheat herbs, is affected by different UV-B radiation levels: the rutin content is lower in plants growing at a level of UV-B light corresponding to 17% ozone depletion. Applied doses of UV-B radiation exert a state of stress, where limits of tolerance are exceeded and adaptive capacity is overtaxed, possibly resulting in a disturbance in rutin synthesis. The measurements suggest that ambient levels of UV-B radiation stimulate rutin accumulation in buckwheat plant compared with reduced UV-B level. The effect is more evident in leaves than in flowers. Enhanced UV-B radiation obstructs rutin accumulation (Samo Kreft et al., Journal of Experimental Botany, Vol. 53, No. 375, pp. 1801-1804, August 2002).

Broad physico-chemical diversity of stress-induced complexes and compounds and absence of universal specific "markers" suggest that capturing all stress-induced biologically active complexes and compounds in a single extract is not possible.

Therefore, there is a need for methods and systems for generating and isolating stress-induced bioactive fractions in photosynthetic plants. The present invention is directed to overcoming these and other deficiencies in the art.

SUMMARY OF THE INVENTION

The present invention is generally directed to biologically active fractions obtained from stress-induced photosynthetic organisms (the biologically active fractions being referred to herein as "BAFSI"). The BAFSI of the present invention have complexes and compounds with desirable target activities that are generated by natural defense mechanisms. The BAFSI can be captured and isolated via fresh plant fractionation technologies and are well suited for their utilization in skin care, sun care, hair care and personal care formulations and applications comprising at least one BAFSI and other cosmetically acceptable ingredients and actives.

In one aspect, the present invention relates to a method for producing a stress-induced photosynthetic organism for use in isolating altered bioactive fractions (i.e., BAFSI). This method involves (i) providing a photosynthetic organism and (ii) cultivating the photosynthetic organism under stress-inducing cultivation conditions effective to produce a stress-induced photosynthetic organism suitable for use in isolating an altered bioactive fraction therefrom. Suitable stress-inducing cultivation conditions include, without limitation, subjecting the photosynthetic organism to a stress factor or to a plurality of stress factors. The stress factor or plurality of stress factors can include, without limitation, stress factors such as ultraviolet light, ozone, osmotic pressure, hydrostatic pressure, and/or a combination thereof. The stress factor or plurality of stress factors used in this method are effective to alter at least one characteristic of at least one bioactive fraction isolated from the stress-induced photosynthetic organism compared to a corresponding bioactive fraction isolated from a non-stress-induced photosynthetic organism. The present invention also relates to a stress-induced photosynthetic organism produced by this method.

In another aspect, the present invention relates to a method for isolating an altered bioactive fraction from a stress-induced photosynthetic organism. This method involves (i) providing a stress-induced photosynthetic organism produced according to the present invention; (ii) separating the stress-induced photosynthetic organism into cell juice and a cell walls component; (iii) treating the cell juice under conditions effective to yield a bioactive fraction, where the bioactive fraction includes, but is not limited to, a cell serum fraction, a membrane fraction, a cell juice supernatant fraction, and a cell serum filtrate fraction; and (iv) isolating the bioactive fraction from the treated cell juice. The isolated bioactive fraction has at least one altered characteristic compared to a corresponding bioactive fraction isolated from a non-stress-induced photosynthetic organism. The present invention also relates to an altered bioactive fraction isolated according to this method.

In another aspect, the present invention relates to a bioactive composition that includes an isolated bioactive fraction derived from a stress-induced photosynthetic organism, where the bioactive fraction includes, but is not limited to, a cell serum fraction, a membrane fraction, a cell juice supernatant fraction, and a cell serum filtrate fraction.

In another aspect, the present invention relates to a bioactive topical formulation suitable for topical application to a mammal, where the bioactive topical formulation includes (i) a topically effective amount of the bioactive composition of the present invention and (ii) a topically acceptable carrier.

In another aspect, the present invention relates to a method for inhibiting inflammatory activity in skin tissue of a mammal. This method involves (i) providing the bioactive composition according to the present invention and (ii) applying the bioactive composition to the skin tissue in an amount effective to inhibit inflammatory activity in the skin tissue.

In another aspect, the present invention relates to a method of protecting skin tissue of a mammal from ultraviolet light-induced damage. This method involves (i) providing the bioactive composition according to the present invention and (ii) applying the bioactive composition to the skin tissue in an amount effective to reduce ultraviolet light-induced damage of the skin tissue and to prevent oxidative damage of the skin tissue.

In another aspect, the present invention relates to a method for normalizing skin disorders in skin tissue of a mammal. This method involves (i) providing the bioactive composition according to the present invention and (ii) applying the bioactive composition to the skin tissue in an amount effective to normalize a cell disorder in the skin tissue.

In another aspect, the present invention relates to a system for cultivating stress-induced photosynthetic organisms. This system includes (i) a bioreactor for cultivating a photosynthetic organism; and (ii) a cultivation control system for controlling cultivation conditions in the bioreactor. The cultivation control system is configured to introduce a stress factor or a combination of two or more stress factors into the bioreactor, and is configured to modulate the intensity, duration, and/or concentration of the stress factor or combination of two or more stress factors in the bioreactor. The stress factor or combination of two or more stress factors include, but are not limited to, a stress factor such as ultraviolet light, ozone, osmotic pressure, hydrostatic pressure, and a combination thereof.

Stress induced biologically active complexes and compounds ("SIBAC") isolated via fresh plant fractionation technologies can also accurately be described as biologically active fractions from stress-induced photosynthetic organisms (abbreviated herein as "BAFSI"). As used herein, the terms "biologically active" and "bioactive" are used interchangeably.

BAFSI contain complexes and compounds that are generated by natural defense mechanisms, which protect photosynthetic organisms (plants, marine organisms) against various stresses and provide subsequent access to all these complexes and compounds and a basis for their evaluation.

It was surprisingly and unexpectedly found that various stress factors, their intensity, and their duration generate modulatory effects (increase, decrease or alteration) on the various characteristics of the BAFSI, including, but not limited to: physico-chemical properties (dry matter content; osmolality, surface tension, surface modification capabilities) and biological activities that include, but are not limited to: enzyme inhibition; antioxidant activity and free radical scavenging.

It was also unexpectedly found that similar stress factors applied to different photosynthetic organisms can produce different effects on the characteristics of BAFSI obtained from these plants.

Various stresses applied to the cultivated photosynthetic organisms induce generation of BAFSI with desirable biological activities and physico-chemical properties, which also can be useful in skin care, sun care, hair care and personal care compositions and applications. For example, BAFSI of the present invention can be used as ingredients regulating activity of certain enzymes (trypsin, elastase, etc.), which play important roles in human skin metabolism, as well as ingredients with antioxidant and free radical scavenging activities. The isolation and screening of prospective BAFSI with the optimal combination of the useful physico-chemical properties and biological activities that include, but are not limited to, antioxidant and free radical scavenging activities; inhibition of enzymes associated with skin ageing and environmental damage, skin protection and repair of human tissues, can create a foundation for developing novel multifunctional ingredients for use in the skin care, sun care, hair care and personal care markets.

The present invention is also related to a process that includes: induction of stresses during cultivation of various photosynthetic organisms, including marine organisms; collection of fresh plant material from stressed plants; its fractionation to isolate core BAFSI enriched with stress-induced biologically active complexes and compounds; identification of BAFSI with desirable target activities; and their utilization in skin care, sun care, hair care and personal care formulations and applications.

In various embodiments of the present invention, generation of BAFSI was initiated by different stress factors which include, but are not limited to, ultraviolet light (UV), ozone ($O_3$), osmotic pressure and the significant change in original cultivation conditions, for example, in hydrostatic pressure. Basic input stress signals include, but are not limited to, impulse function ($f(t)=\delta(t)$, unit step function ($f(t)=u(t)$), and ramp function ($f(t)=t$).

Photosynthetic organisms of the present invention include, but are not limited to, aquatic photosynthetic organisms that are valuable sources of ingredients with various biological activities.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
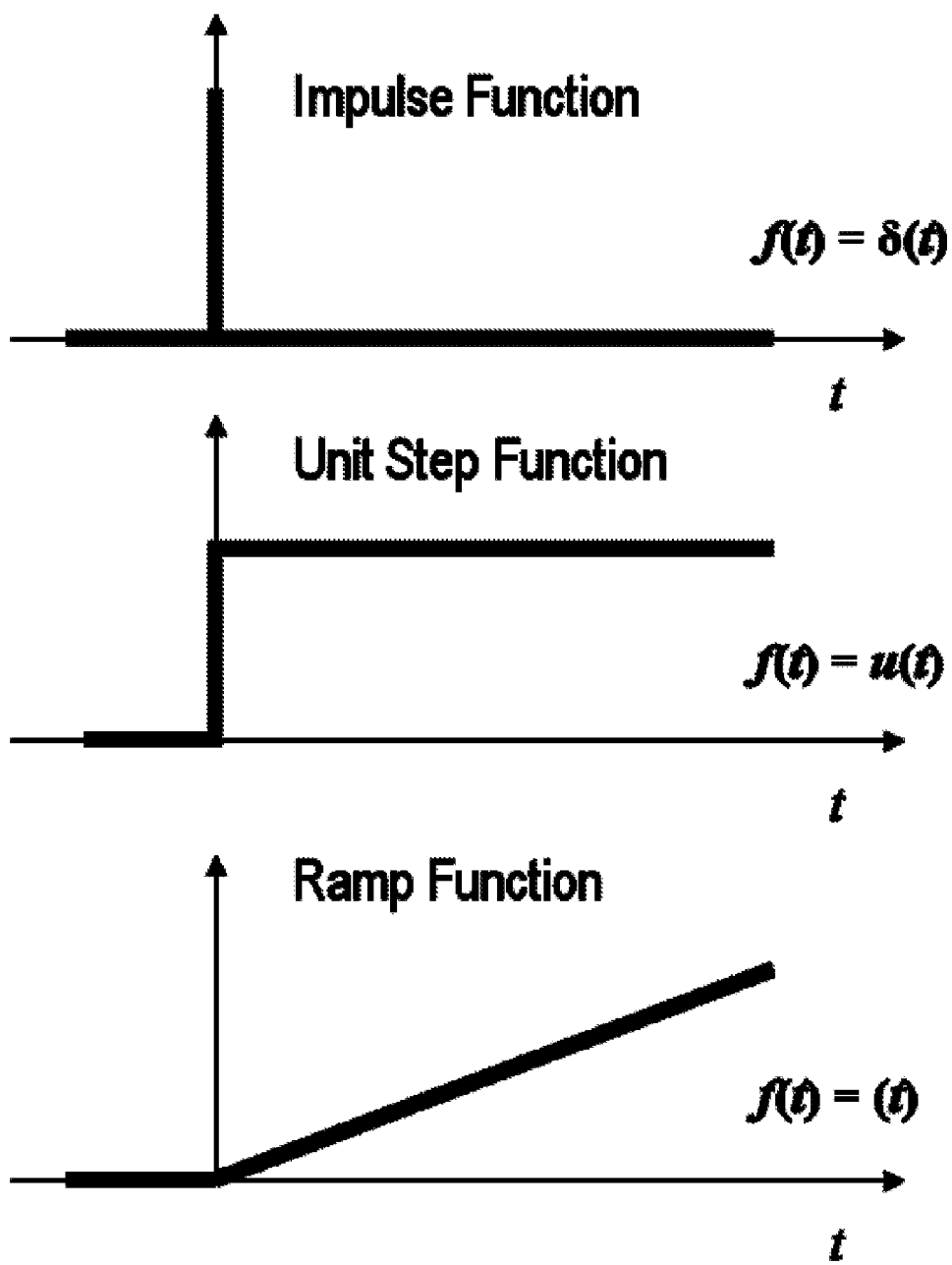
FIG. 1 is a schematic illustrating various functions used for applying stresses (i.e., stress factors) according to various embodiments of the present invention.

The present invention generally relates to biologically active fractions from stress-induced photosynthetic organisms, the bioactive fractions of the present invention being referred to herein by the abbreviation "BAFSI." BAFSI of the present invention contain complexes and compounds with target biological activities, and are generated by natural defense mechanisms of photosynthetic organisms that are captured and isolated via fresh plant fractionation technologies. BAFSI are well suited for their utilization in skin care, sun care, hair care, and personal care formulations and applications.

The present invention also relates to skin care, sun care, hair care and personal care compositions comprising (a) at least one BAFSI and (b) other cosmetically acceptable ingredients and actives.

The present invention further relates to topically applicable cosmetic or dermatological compositions well suited for the UV-photoprotection of human skin and/or hair comprising an effective UV-photoprotecting amount of: (a) at least one UV screening agent; (b) at least one BAFSI; and (c) other cosmetically acceptable ingredients and functional polymers.

Provided herein below are additional aspects of the present invention, including additional details that are suitable for one of ordinary skill in the art to make and use these aspects of the present invention.

The present invention relates to a method for producing a stress-induced photosynthetic organism for use in isolating altered bioactive fractions (i.e., BAFSI). This method involves (i) providing a photosynthetic organism and (ii) cultivating the photosynthetic organism under stress-inducing cultivation conditions effective to produce a stress-induced photosynthetic organism suitable for use in isolating an altered bioactive fraction therefrom.

As used herein, an altered bioactive fraction of the present invention refers to a bioactive fraction isolated from a stress-induced photosynthetic organism, where that bioactive fraction has at least one altered characteristic compared to a corresponding bioactive fraction isolated from a non-stress-induced photosynthetic organism. An altered characteristic is as described herein, including, without limitation, altered physico-chemical properties, altered surface modification properties, altered moisturization properties, altered anti-inflammatory activity, and/or altered anti-ageing activity. In a particular embodiment, an altered characteristic improves a bioactivity or a property of the bioactive fraction of the present invention compared to the bioactivity or property of a corresponding bioactive fraction from a non-stress-induced photosynthetic organism. In another embodiment, the at least one altered characteristic refers to a change of one or more bioactivities or properties of the bioactive fraction of the present invention compared to the bioactivities or properties of a corresponding bioactive fraction from a non-stress-induced photosynthetic organism.

Suitable stress-inducing cultivation conditions are as described herein and can include, without limitation, subjecting the photosynthetic organism to a stress factor or to a plurality of stress factors. As set forth herein, the stress factor or plurality of stress factors can include, without limitation, stress factors such as ultraviolet light, ozone, osmotic pressure, hydrostatic pressure, and/or a combination thereof. As set forth herein, the stress factor or plurality of stress factors are effective to alter at least one characteristic of at least one bioactive fraction isolated from the stress-induced photosynthetic organism compared to a corresponding bioactive fraction isolated from a non-stress-induced photosynthetic organism.

The method of the present invention for producing a stress-induced photosynthetic organism is effective to alter at least one characteristic of the bioactive fractions of the present invention, including, without limitation, characteristics such as physico-chemical properties, surface modification properties, moisturization properties, anti-inflammatory activity, and/or anti-ageing activity.

As used herein, the physico-chemical properties include, but are not limited to, properties such as surface tension, dry matter content, and osmolality.

As used herein, anti-inflammatory and/or anti-ageing activities include, but are not limited to, activities such as elastase inhibition, trypsin inhibition, anti-oxidant activity, and free-radical scavenging activity.

Bioactive fractions that can be isolated from the stress-induced photosynthetic organism can include, without limitation, a cell serum fraction, a membrane fraction, a cell juice supernatant fraction, and a cell serum filtrate fraction.

The present invention also relates to a stress-induced photosynthetic organism produced by this method.

As used herein, a photosynthetic organism includes aquatic photosynthetic organisms and terrestrial non-aquatic photosynthetic organisms. Any organism that has photosynthetic activity can be used in the present invention.

According to the present invention, an aquatic photosynthetic organism includes, but is not limited to, aquatic photosynthetic organisms of the Phaeophyceae and Chlorophyceae classes. In particular, the aquatic photosynthetic organism can include, without limitation, species of the *Macrocystis* and *Chaetomorpha* genera. Suitable species of the *Macrocystis* genus can include, without limitation, *Macrocystis angustifolia, Macrocystis integrifolia, Macrocystis laevis*, and *Macrocystis pyrifera*. Suitable species of the *Chaetomorpha* genus can include, without limitation, *Chaetomorpha aerea, Chaetomorpha antermina, Chaetomorpha basiretorsa, Chaetomorpha brachygona, Chaetomorpha californica, Chaetomorpha cannabina, Chaetomorpha crassa, Chaetomorpha gracilis, Chaetomorpha linum, Chaetomorpha melagonium, Chaetomorpha natalensis*, and *Chaetomorpha spiralis*.

The present invention also relates to a method for isolating an altered bioactive fraction from a stress-induced photosynthetic organism. This method involves (i) providing a stress-induced photosynthetic organism produced according to the present invention; (ii) separating the stress-induced photosynthetic organism into cell juice and a cell walls component; (iii) treating the cell juice under conditions effective to yield a bioactive fraction, where the bioactive fraction includes, but is not limited to, a cell serum fraction, a membrane fraction, a cell juice supernatant fraction, and a cell serum filtrate fraction; and (iv) isolating the bioactive fraction from the treated cell juice.

In one embodiment, the bioactive fractions and the stress-induced complexes and compounds in the stress-induced photosynthetic organism of the present invention can be captured and isolated via fresh plant fractionation technologies which are described in the following U.S. patents and published patent applications: U.S. Pat. Nos. 7,537,791, 7,442,391, and 7,473,435; and U.S. Patent Application Publication Nos. US2007/0196523, US2009/0186109, US2009/0185990 and US2009/0017144, the disclosures of which are hereby incorporated by reference herein in their entirety.

In view of the isolation techniques described herein and in view of the fresh plant fractionation technologies taught in the above U.S. patents and published patent applications, one of ordinary skill in the art can readily determine how to produce the isolated bioactive fractions of the present invention. For reference purposes, below is a brief synopsis of the teachings of each of the above-cited U.S. patents and published patent applications.

U.S. Pat. No. 7,537,791 discloses parthenolide free bioactive ingredients from feverfew (*Tanacetum parthenium*) and processes for their production, which is incorporated herein by reference.

U.S. Pat. No. 7,442,391 discloses bioactive botanical cosmetic compositions and processes for their production, which is incorporated herein by reference.

U.S. Pat. No. 7,473,435 discloses bioactive compositions form Theacea plants and processes for their production and use, which is incorporated herein by reference.

U.S. Application Publication No. 2007/0196523 discloses parthenolide free bioactive ingredients from feverfew (*Tanacetum parthenium*) and processes for their production, which is incorporated herein by reference.

U.S. Application Publication No. 2009/0186109 discloses parthenolide free bioactive ingredients from feverfew (*Tanacetum parthenium*) and processes for their production, which is incorporated herein by reference.

U.S. Application Publication No. 2009/0185990 discloses bioactive compositions form Theacea plants and processes for their production and use, which is incorporated herein by reference.

U.S. Application Publication No. 2009/0017144 discloses bioactive botanical cosmetic compositions and processes for their production, which is incorporated herein by reference.

As one of ordinary skill in the art can appreciate, these fractionation and isolation technologies provide means to completely capture all intracellular material and distribution of all its components among core fractions, which are isolated from fresh plant material without any external solvents or chemicals and without damaging of intracellular osmotic pressure homeostasis. As a result, the integrity of all organelles and cytoplasm components of photosynthetic organisms subjected to various stress factors can be completely preserved and isolated in various fractions.

The isolated bioactive fractions produced by the isolation method of the present invention have at least one altered characteristic compared to a corresponding bioactive fraction isolated from a non-stress-induced photosynthetic organism. As noted herein, examples of the characteristics that can be altered in the isolated bioactive fractions can include, without limitation, physico-chemical properties, surface modification properties, moisturization properties, anti-inflammatory activity, and anti-ageing activity.

The present invention also relates to a bioactive composition that includes an isolated bioactive fraction derived from a stress-induced photosynthetic organism, where the bioactive fraction includes, but is not limited to, a cell serum fraction, a membrane fraction, a cell juice supernatant fraction, and a cell serum filtrate fraction.

The bioactive fraction used in the bioactive composition is isolated from a stress-induced photosynthetic organism that has been subjected to a stress factor or to a plurality of stress factors under conditions effective to alter at least one characteristic of the isolated bioactive fraction compared to a corresponding bioactive fraction isolated from a non-stress-induced photosynthetic organism. The altered characteristics and the various stress factors are as provided herein.

In one embodiment, the bioactive composition can also include a stabilizing agent. Stabilizing agents suitable for use in the bioactive composition of the present invention are well known in the art. Examples of suitable stabilizing agents include, but are not limited to, emulsifiers, preservatives, antioxidants, polymer matrices, and mixtures thereof.

In one embodiment, the bioactive fraction is substantially free of undesirable components that include, but are not limited to, proteins. Absence of proteins is important because residual proteins may cause contact dermatitis (V. Janssens, et al., "Protein contact dermatitis: myth or reality?", British Journal of Dermatology 1995; 132: 1-6). Additionally, presence of proteins can create stability and compatibility issues with formulation of finished products.

The present invention also relates to a bioactive topical formulation suitable for topical application to a mammal, where the bioactive topical formulation includes (i) a topically effective amount of the bioactive composition of the present invention and (ii) a topically acceptable carrier.

Topically acceptable carriers suitable for use in the bioactive composition of the present invention are well known in the art. A suitable topically acceptable carrier can include, without limitation, a hydrophilic cream base, a hydrophilic lotion base, a hydrophilic surfactant base, a hydrophilic gel base, a hydrophilic solution base, a hydrophobic cream base, a hydrophobic lotion base, a hydrophobic surfactant base, a hydrophobic gel base, and a hydrophobic solution base.

In various embodiments, the bioactive fractions, compositions, and formulations of the present invention are "cosmetically acceptable." As used herein, the term "cosmetically acceptable" refers to bioactive fractions, compositions, ingredients, formulations, cosmetically active agents, or inert ingredients that are suitable for use in contact with mammalian tissues (e.g., the skin of humans) without undue toxicity, incompatibility, instability, irritation, allergic response, and the like, commensurate with a reasonable benefit/risk ratio.

In various embodiments, the bioactive fractions, compositions, and formulations of the present invention are useful for topical application to humans, and can be applied in a "safe and effective amount." As used herein, the term "safe and effective amount" refers to an amount of bioactive fraction, composition, ingredient, or formulation sufficient to significantly induce a positive modification in the condition to be regulated or treated, but low enough to avoid serious side effects. The safe and effective amount of the bioactive composition, ingredient or formulation containing the bioactive fraction will vary with the particular condition being treated, the age and physical condition of the end user, the severity of the condition being treated/prevented, the duration of the treatment, the nature of concurrent therapy, the specific bioactive ingredient or formulation employed, the particular cosmetically-acceptable topical carrier utilized, and like factors.

The formulations containing the bioactive fractions or compositions of the present invention may be prepared using methodology that is well known by an artisan of ordinary skill.

The bioactive topical formulation can be formulated so that the bioactive composition is present in an amount ranging from between about 0.01 percent and about 98.0 percent of the total weight of the bioactive topical formulation. The present invention contemplates bioactive topical formulations having concentrations of the bioactive composition that fall within the stated range of 0.01 to 98.0 percent, including the terminal points (i.e., 0.01 and 98.0 percent). One of ordinary skill in the art can readily determine the concentration of bioactive composition suitable for use in a particular topical formulation.

The bioactive topical formulation of the present invention is suitable for use in various applications, including, for example, skin care applications, sun care applications, hair care applications, and personal care applications. One of ordinary skill in the art can readily determine other uses of the bioactive topical formulation in other applications.

The bioactive topical formulation of the present invention is suitable for use as a lotion, including, without limitation, a skin lotion, a sun protective gel, a moisturizing lotion, a sunscreen lotion, a facial gel lotion, a facial toning lotion, and an anti-ageing lotion. One of ordinary skill in the art can readily determine other lotions that can incorporate the bioactive topical formulation of the present invention.

The present invention also relates to a method for inhibiting inflammatory activity in skin tissue of a mammal. This method involves (i) providing the bioactive composition according to the present invention and (ii) applying the bioactive composition to the skin tissue in an amount effective to inhibit inflammatory activity in the skin tissue. One of ordinary skill in the art can readily determine the parameters and other specific protocols for providing and applying the bioactive composition of the present invention in accordance with this method.

The present invention further relates to a method of protecting skin tissue of a mammal from ultraviolet light-induced damage. This method involves (i) providing the bioactive composition according to the present invention and (ii) applying the bioactive composition to the skin tissue in an amount effective to reduce ultraviolet light-induced damage of the skin tissue and to prevent oxidative damage of the skin tissue. One of ordinary skill in the art can readily determine the parameters and other specific protocols for providing and applying the bioactive composition of the present invention in accordance with this method.

The present invention also relates to a method for normalizing skin disorders in skin tissue of a mammal. This method involves (i) providing the bioactive composition according to the present invention and (ii) applying the bioactive composition to the skin tissue in an amount effective to normalize a cell disorder in the skin tissue. Cell disorders in the skin tissue are well known in the art. One of ordinary skill in the art can readily determine the parameters and other specific protocols for providing and applying the bioactive composition of the present invention in accordance with this method.

As used herein, the term "mammal" includes, but is not limited to, humans.

The present invention also relates to a system for cultivating stress-induced photosynthetic organisms. This system includes (i) a bioreactor for cultivating a photosynthetic organism; and (ii) a cultivation control system for controlling cultivation conditions in the bioreactor. The cultivation control system is configured to introduce a stress factor or a combination of two or more stress factors into the bioreactor, and is configured to modulate the intensity, duration, and/or concentration of the stress factor or combination of two or more stress factors in the bioreactor. The stress factor or combination of two or more stress factors include, but are not limited to, a stress factor such as ultraviolet light, ozone, osmotic pressure, hydrostatic pressure, and a combination thereof.

Figure 17:
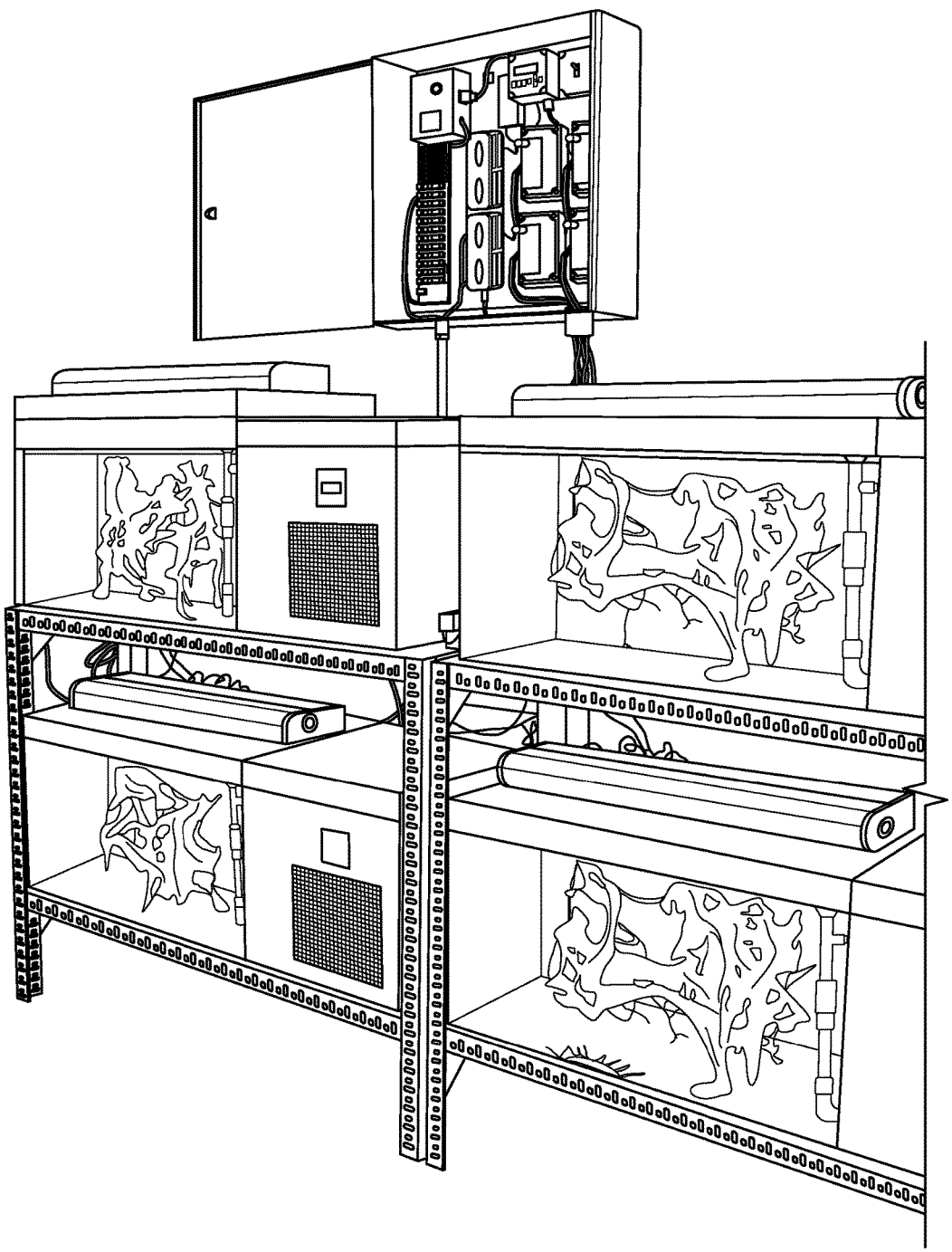
FIG. 17 is a photograph of one embodiment of the system of the present invention. The system is shown as being effective for cultivating aquatic photosynthetic organisms in controlled conditions and applying various stress factors.

In one embodiment, the system of the present invention is used for cultivating an aquatic photosynthetic organism, where the bioreactor is configured for cultivating the aquatic photosynthetic organism in a liquid medium. An example of a suitable configuration of the system for use with aquatic photosynthetic organisms is illustrated in FIG. 17. In a particular embodiment, the bioreactor can be, without limitation, an aquarium. Various components of one embodiment of the system of the present invention are set forth in Table 1 (herein below). In view of the teachings herein, one of ordinary skill in the art can readily determine other general or specific components suitable for use in the system of the present invention, and such other general or specific components are therefore contemplated by the present invention.

Set forth herein below are additional details regarding the various aspects and embodiments of the present invention.

In one embodiment, giant brown kelp (*Macrocystis pyrifera*) was selected due to its fast growth rate and ability to survive at extreme conditions, particularly at high pressure and relatively low temperature. It is found off the coasts of several continents around the world, for example, off the west coast of North America, from southern Alaska to Baja Calif.; off the coast of South America, South Africa, and southern Australia. In order for giant kelp to flourish in a particular environment, it must have a hard surface for attachment, high nutrient concentration, moderate water motion, and clear and clean ocean water. *Macrocystis* prefers salty, well-mixed salty water in the outer coastal waters (Connor J, Baxter C, Kelp Forest. Monterey Bay Aquarium Foundation, Monterey: 1989). Giant brown kelp is a rich source of iodine, calcium, and sulfur, and a good source of iron, phosphorus, sodium, potassium, magnesium, and the vitamins A, D, E, K, and B complex. The main constituents of kelp are: mucopolysaccharides, alginates, phenolic compounds, polar lipids, and glycosyl ester diglycerides, as well as protein, carbohydrates, essential fatty acids, amino acids, and about thirty minerals, chlorophyll a and c, as well as carotenes and xanthophylls (Wurges, J., and R. J. Frey. 2005. In J. L. Longe, The Gale Encyclopedia of Alternative Medicine, Farmington Hills, Mich.: Thomson/Gale. ISBN 0787693960). Cell walls are composed of cellulose layered with polysaccharide (such as the valuable alginic acid).

Giant kelp stipes are similar to stems of terrestrial plants. The essential sugars produced in photosynthesis are used to fuel their own metabolic needs, as well as transport them to other parts of the algae, including the holdfast, spore producing blades, and new fronds.

Giant brown kelp blades are the site where most of the sun's light energy is captured and converted into sugars by photosynthesis; sugars produced are then used by the algae for energy. Giant brown kelp pneumatocysts are gas-filled bladders that act as buoys to raise the blades closer to the surface where photosynthesis can occur (Bold H C, Wynne M J. Introduction to the Algae. Prentice Hall, Englewood Cliffs: 1978).

A giant kelp holdfast in appearance looks similar to roots. However, these roots do not uptake nutrients and water as terrestial plants do. The holdfast maintains the kelp's position. The holdfast of giant kelp is perennial, and will last one to seven years (Connor J, Baxter C, Kelp Forest. Monterey Bay Aquarium Foundation, Monterey: 1989).

In another embodiment, green algae (*Chaetomorpha linum*) were selected due to its fast growth rate, its ability to survive at relatively high temperature and its high level of photosynthetic activity relative to *Macrocystis pyrifera*. *Chaetomorpha linum* is found in relatively shallow sub tropical to tropical Pacific Ocean reefs. It is a free floating algae that grows in filamentous clumps without attachment to any substrate. *Chaetomorpha linum* is frequently aqua cultured for use as a natural filter to remove impurities, especially nitrates.

In another embodiment, generation of BAFSI was initiated by different stress factors which include, but are not limited to, ultraviolet light (UV), ozone ($O_3$), osmotic pressure (Biological Control Systems Analysis. John H. Milsum—McGraw-Hill Book Company NY, 1966), and the significant change in original cultivation conditions, for example, in hydrostatic pressure.

Figure 2:
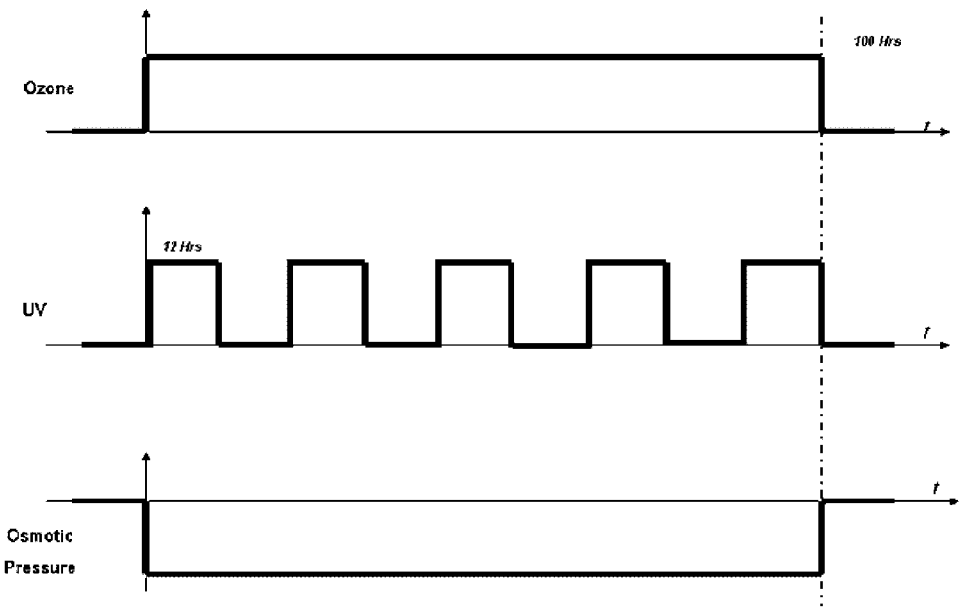
FIG. 2 is a schematic showing the functions describing stresses applied to aquatic organisms according to various embodiments of the present invention. In the case of Giant brown kelp (Macrocystis pyrifera), there is an additional factor of hydrostatic stress, as cultivation in aquariums provides less water pressure than common for natural growth conditions for the species. Hydrostatic stress begins when the kelp is removed from its normal environment and ends with the end of the experiment. It is a factor that applies to all of the kelp in the experiment equally and is thus not shown.

In one embodiment, basic input stress signals presented in FIG. 1 include, but are not limited to, impulse function ($f(t)=\delta(t)$), unit step function ($f(t)=u(t)$), and ramp function ($f(t)=t$). The functions describing stresses applied to algae are shown in FIG. 2.

In another embodiment, in case of Giant Kelp, there is an additional factor of hydrostatic stress, as cultivation in aquariums provides less water pressure than common for natural growth conditions for the species. Hydrostatic stress begins when the kelp is removed from its normal environment and ends with the end of the experiment. It is a factor that applies to all of the kelp in the experiment equally and is thus not shown.

Cultivation Conditions and Parameters

In one embodiment of the present invention, four identical 150 liter aquariums were allowed to cycle for 14 days with 35 g/l artificial sea salt. Then Proline F/2 algae food was added to each aquarium and maintained by monitoring the nitrate level during the course of cultivation. Detailed information related to the equipment components of this embodiment is presented in Table 1.

TABLE 1

| Description of Cultivation Equipment and Control System Components | |
|---|---|
| Components | Description and Manufacturer |
| Aquarium Design | West Coast Aquatics Mini Ocean 18" × 48" × 18" with integrated filtration and conditioning chamber including a W. C. Aquatics 1/4 hp chiller, Penguin 1140 powerhead, Krypton 700 air pump, and W.C. Aquatics 300 W Silver Series heater (West Coast Aquatics, CA) |
| Lighting System | Current 30" Dual Satellite compact fluorescent fixtures with 65 W Dual Daylight 6,700/10,000 K bulb and 65 W Dual Actinic 420/460 nm bulb (Current-USA, CA) |

TABLE 1-continued

Description of Cultivation Equipment and Control System Components

| Components | Description and Manufacturer |
| --- | --- |
| Wave Maker | 2 - Penguin 1140 powerheads (Marineland, CA) |
| Aquarium Control System | OMB-DAQ-56 20 Channel 22 Bit Data Acquisition System with OMB-PDQ1 20 Channel Expansion Module and 12 ACO5-C Digital I/O Modules for 3A AC output, with attached computer running DASYLAB Software (Omega Engineering, Inc., CT) |
| Conductivity Probe | CDE-300 (Omega Engineering, Inc., CT) |
| pH Probe | Omega PHE-7351-15 (Omega Engineering, Inc., CT) |
| Redox Probe | Omega ORE-1311 (Omega Engineering, Inc., CT) |
| Temperature Probe | Omega KTXL-14U-12 T/C (Omega Engineering, Inc., CT) |
| Dissolved Oxygen Meter | Hanna HI 9143 (Hanna Instruments, RI) |
| $O_3$ Generator | Adjustable output from 0 to 200 mg/hr. Aquazone Plus 200 (Red Sea, TX) |
| Air Pump for $O_3$ system | Whisper AP 150 - 150 lph (Tetra US, VA) |
| $O_3$ Injector and Mixer | MX-500P Ozone Static Mixer and MK-584 Kynar Injector (Ozone Solutions, Inc., IA) |
| Water Pump for $O_3$ system | Eheim 1250 - 720 lph (Eheim GmbH, Germany) |
| $O_3$ Sensor/Analyzer | Analog Plus Ozone Sensor with AV88 Dissolved Ozone Analyzer (Aquasensors, WI) |
| UV Source | XX-15MR bench lamp, MR 302 nm, 15 W (UVP LLC, CA); 2 fixtures, each with two bench lamps |
| UV Meter | Model UVX Digital Radiometer (Part # 97-0015-02) with Model UVX-31 (Part # 97-0016-04) midrange sensor (UVP LLC, CA) |
| Test Kits | API For $NH_3/NH_4$, $NO_2$, $NO_3$, $PO_4$, $Ca^{2+}$, KH (Mars Fishcare, Inc., PA) |

The utilized compact fluorescent lighting system modeled the properties of natural sunlight at surface and subsurface conditions. The UV source modeled radiation in the UVB region. Wave makers provided water flow and turbulence to simulate natural environmental conditions. A control system monitored pH, redox potential, conductivity, ozone concentration and temperature. Additionally, timers controlled lighting, UV and ozone systems. Osmolality, refractive index, and specific gravity along with levels of ammonia, nitrite, nitrate, phosphate, calcium and carbonate hardness (KH) were also monitored. One aquarium was always used as control and three others were used to introduce (a) three different levels of selected stress factor or (b) three different types of stress factors.

Set forth in FIG. 17 is a photo of these aquariums with cultivated Giant brown kelp (*Macrocystis pyrifera*).

In one embodiment, UVB stress in aquariums was applied with external UVB lights. Two 30 Watt UVB light fixtures were installed over the aquariums and intensity of UVB was measured with a UVX Radiometer. Ozone stress in aquariums was introduced by injection of ozone into the aquariums with the system described in Table 1. Aquariums without ozone generation also had the same ozone injection system installed to eliminate differences in air and water flow. Dissolved Ozone concentration was measured with Aquasensors Ozone Sensor and Analyzer. Osmotic stress in aquariums was introduced via regulation of salt water concentration. The osmolality was measured with Model 3250 freezing point depression Osmometer (Advanced Instruments, Inc., MA). Hydrostatic stress (reduced hydrostatic pressure conditions) in aquariums was in effect for Giant brown kelp, which typically grow in deeper water (10 ft or deeper). The ranges of cultivation parameters used for control and stressed systems stress factors and their parameters are presented in Table 2.

TABLE 2

Ranges of Cultivation Parameters Used for Control and Stressed Aquariums

| Cultivation Parameter | Control | Ozone Stress | Osmotic Stress | UV Stress | Hydrostatic Stress*** |
| --- | --- | --- | --- | --- | --- |
| pH | 8.0-8.3 | 8.0-8.3 | 8.0-8.3 | 8.0-8.3 | 8.0-8.3 |
| Conductivity (S/m) | 4.6-5.1 | 4.6-5.1 | 3.5-6.0 | 4.6-5.1 | 4.6-5.1 |
| Temperature (C.) | * | * | * | * | * |
| Redox potential | 150-250 | 200-400 | 150-250 | 150-250 | 150-250 |
| Dissolved $O_2$ (mg/l) | 7.0-8.0 | 7.0-9.0 | 7.0-8.0 | 7.0-8.0 | 7.0-8.0 |
| Refractive Index (nD) | 1.3385-1.3395 | 1.3385-1.3395 | 1.3370-1.3410 | 1.3385-1.3395 | 1.3385-1.3395 |
| Osmolality (mOs/kg) | 900-1040 | 900-1040 | 600-1200 | 900-1040 | 900-1040 |
| $NH_3/NH_4$ (mg/l) | 0 | 0 | 0 | 0 | 0 |
| $NO_2$ (mg/l) | 0 | 0 | 0 | 0 | 0 |
| $NO_3$ mg/l | 120-160 | 120-160 | 120-160 | 120-160 | 120-160 |
| $PO_4$ (mg/l) | 2.5-5.0 | 2.5-5.0 | 2.5-5.0 | 2.5-5.0 | 2.5-5.0 |
| $Ca^{2+}$ (mg/l) | 400-480 | 400-480 | 400-480 | 400-480 | 400-480 |
| $CO_3^{2-}$ (mg/l) | 140-200 | 140-200 | 140-200 | 140-200 | 140-200 |

TABLE 2-continued

Ranges of Cultivation Parameters Used for Control and Stressed Aquariums

| Cultivation Parameter | Control | Ozone Stress | Osmotic Stress | UV Stress | Hydrostatic Stress*** |
|---|---|---|---|---|---|
| Specific Gravity (g/cm$^3$) | 1.023-1.027 | 1.023-1.027 | 1.017-1.018 | 1.023-1.027 | 1.023-1.027 |
| Lighting Cycle (h/d) | ** | ** | ** | ** | ** |
| UVB Light (mW/cm$^2$ at 302 nm) | 0 | 0 | 0 | 1 or 2** | 0 |

Notes:
*Temperature depends on species (for kelp T = 12.5° C.; for green algae T = 25° C.)
**Lighting cycle can be varied from 0 to 24 hours/day. For daylight cycle, typically 12 hours/day. For UVB lighting from 3 hrs/day to 12 hours/day.
***Hydrostatic stress occurs when algae, which typically grow in deeper water (10 ft or deeper), for example, Giant brown kelp (*Macrocystis pyrifera*), are transferred and then cultivated in more shallow reservoirs (aquariums) with reduced hydrostatic pressure compared to that in original conditions.

In one embodiment, the ranges of cultivation parameters used for control and stressed systems with Giant brown kelp (*Macrocystis pyrifera*) were as follows: Cultivation times were 72 hrs (3 days) or 96 hrs (4 days). Control (No stress): Giant brown kelp (*Macrocystis pyrifera*) was harvested from original cultivation conditions in deeper water and processed without being transferred to an aquarium; Hydrostatic pressure stress only was on-going during respective cultivation times; Hydrostatic stress occurs when algae, which typically grow in deeper water (10 ft or deeper), for example, Giant brown kelp (*Macrocystis pyrifera*), are transferred and then cultivated in more shallow reservoirs (aquariums) with reduced hydrostatic pressure compare to the one existing in original cultivation conditions; Hydrostatic Stress+UVB Stress=2 mW/cm$^2$ UVB 3-12 hrs/day; Hydrostatic Stress+Ozone Stress=100 mg/hr continuous injection; Hydrostatic Stress+Osmotic Stress–osmolality of cultivation media=75% of control. Cultivation times were: 72 hrs (3 days) or 96 hrs (4 days).

In one embodiment, the ranges of cultivation parameters used for control and stressed systems with Green algae (*Chaetomorpha linum*) that typically grow in shallow water and thus do not experience hydrostatic stress in the experiment were as follows: Cultivation times were 24 hrs (1 day), 96 hrs (4 days), 288 hrs (12 days), 456 hrs (19 days). Control (No stress). UVB Stress=2 mW/cm$^2$ UVB 12 hrs/day; Ozone Stress=100 mg/hr continuous injection. Osmotic Stress–osmolality of cultivation media=85% of control.

DEFINITIONS AND METHODS

Set forth below are various definitions of characteristics that can be determined for the bioactive fractions of the present invention, and related methods for measuring or analyzing these characteristics.

Surface Tension

Surface tension is defined as the force along a line of unit length, where the force is parallel to the surface but perpendicular to the line. Surface tension is measured in forces per unit length, its SI unit is N/m (Newtons per meter) (Pierre-Gilles de Gennes; Françoise Brochard-Wyart; David Quéré (2002). Capillary and Wetting Phenomena—Drops, Bubbles, Pearls, Waves. Springer. ISBN 0-387-00592-7; White, Harvey E. (1948). Modern College Physics. van Nostrand. ISBN 0442294018).

Surface tension is caused by the attraction between the liquid's molecules by various intermolecular forces. In the bulk of the liquid, each molecule is pulled equally in every direction by neighboring liquid molecules, resulting in a net force of zero. At the surface of the liquid, the molecules are pulled inwards by other molecules deeper inside the liquid and are not attracted as intensely by the molecules in the neighboring medium (be it vacuum, air or another liquid). Therefore, all of the molecules at the surface are subject to an inward force of molecular attraction which is balanced only by the liquid's resistance to compression, meaning there is no net inward force. However, there is a driving force to diminish the surface area. Thus, the liquid squeezes itself together until it has the locally lowest surface area possible. As a result of surface area minimization, a surface will assume the smoothest shape it can. Since any curvature in the surface shape results in greater area, a higher energy will also result. Consequently, the surface will push back against any curvature in much the same way as a ball pushed uphill will push back to minimize its gravitational potential energy.

Surface tension measurements were performed using a Krüss EasyDrop drop shape analysis system with attached computer running Krüss DSA1 software for device control, image acquisition and analysis of drop shape images. Disposable 2 mL syringes with 1.8 mm diameter disposable dosing needles were used to hold and dispense the samples, with new syringe and new needle for every different sample material. The procedure for performing the measurement is described in Krüss Software for prop Shape Analysis DSA1 v 1.91 User Manual as supplied with the system. Room lighting was adjusted to eliminate bright and non-diffuse light, thus preventing reflections on drop surface. System was turned on, backlight set to 25% intensity, syringe and needle positioned for needle image to take up ~10% of the frame. Focus was adjusted so sharpness as determined by software was maximum achievable. Region of interest was defined with a hanging drop of deionized water. Drop type was set to hanging drop. Image magnitude was read as per needle diameter. Immersion medium density was entered as air density at room temperature at sea level. Water was used for initial control measurement. For water, and for each sample material, sample density was entered, and then volume necessary to produce a properly shaped pendant drop was determined. Following that, surface tension was measured on three pendant drops, a fresh drop for every measurement. Young-Laplace drop contour fit was used for calculation. The mean of the three measurements was considered as the surface tension of a given sample material.

Osmolality

Osmolality is the measure of solute concentration, defined as the number of osmoles of solute per kg of solution. Osmolality measures the number of osmoles of solute particles per unit mass of solution. Osmolality is distinct from molarity because it measures moles of solute particles rather than moles of solute. The distinction arises because some compounds can dissociate in solution, whereas others cannot. Ionic compounds, such as salts, can dissociate in solution into their constituent ions, so there is not a one-to-one relationship between the molality and the osmolality of a solution. For example, sodium chloride (NaCl) dissociates into $Na^+$ and $Cl^-$ ions. Thus, for every 1 mole of NaCl in solution, there are 2 osmoles of solute particles (i.e., a 1 M NaCl solution is a 2 Osm NaCl solution). Both sodium and chloride ions affect the osmotic pressure of the solution. Nonionic compounds do not dissociate, and form only 1 osmole of solute per 1 mole of solute. For example, a 1 M solution of glucose is 1 Osm (Widmaier, Eric P.; Hershel Raff, Kevin T. Strang (2008). Vander's Human Physiology, 11th Ed. McGraw-Hill. pp. 108-112). Osmometer, model 3250 (Advanced Instruments, Inc) was used to determine osmolalities of BAFSI. This instrument utilizes freezing point depression as measuring principle. Freezing point is a colligative property that is dependent on the presence of dissolved particles and their number, but not their identity. The freezing point depression happens both when the solute is an electrolyte, such as various salts, and a non-electrolyte, such as carbohydrates.

Dry Matter

Dry matter reflects the concentration of non volatile components in BAFSI. Dry matter levels were determined by comparing the weight of liquid sample with weight of residual dry matter after liquid components have been evaporated. Disposable aluminum weighing dishes (VWR 25433-016), Ohaus Explorer E00640 balance (Ohaus Corporation) and Shel Lab model 1400E oven (VWR) set at 105 C were utilized. Dry matter percentage is calculated as ('tare+dry'–'tare')/('tare+wet'–'tare')*100.

Vitro Skin (N-19) Surface Modification after Application of BAFSI

A test methodology that utilizes measurements of the contact angle of water to quantify the effects of various substances on the surface properties of a skin-substitute substrate (Correlating Water Contact Angles and Moisturization/Sensory Claims" by Olga V. Dueva-Koganov et al. Cosmetics & Toiletries, January 2007, Vol. 122, No. 1, pp. 20-27) was employed. The data presented in this article show that contact angle measurements can be used to quantify and compare the effects of skin care products on the surface properties of this skin-like substrate. Products that generate lower contact angles (less than 80 deg.) tend to make more sensory claims related to light and non-greasy feel, and short-term moisturization, while products that produce relatively high contact angles tend to make more claims related to long-term moisturization.

Contact angles were measured according to sessile drop method using Krüss EasyDrop drop shape analysis system with attached computer running Krüss DSA1 software for device control, image acquisition and analysis of drop shape images (www.kruss.de/en/products/contact-angle/easydrop.html).

Deionized water was used as a probe solution and Vitro Skin (N-19) from IMS, Inc. as a substrate. Application dose of test BAFSI was 2 mg/sq. cm that is similar to the topical application dose of products used in various skin studies in vivo.

Elastase Inhibition

Elastase is an enzyme that is capable of degrading a number of proteins including elastin, an elastic substance in the skin that supports its structural framework. Elastase is involved in skin inflammation, ageing, photoageing, wrinkle formation, etc. Elastase inhibitory activity was determined by a kinetic colorimetric assay adapted for use with 96-well microtiter plates (Corning 3641) from Corning Incorporated (Corning, N.Y.) and Synergy 2 microplate reader from BioTek Instruments, Inc. (Winooski, Vt.). Enzymatic activity in cleaving the substrate was indicated by a development of yellow color measured as increase in absorbance at 410 nm wavelength. The mean of maximum rates of absorbance increase for negative control wells was considered as 100% of enzyme activity, and $IC_{50}$ was calculated as concentration of sample in the well necessary to reduce the enzyme activity to 50%. Lower $IC_{50}$ values indicate higher elastase inhibition activity. The N-Methoxysuccinyl-Ala-Ala-Pro-Val-pNA substrate (EPC FH237), and elastase (EPC SE563) were obtained from EPC (Elastin Products Company, Inc., Owensville, Mo.). Reaction volume in each well was 200 μA, with concentration of elastase equal to 0.87 units/ml, and substrate equal to 363 μM. This procedure was adapted from method titled "Assay with N-MeO-Suc-Ala-Ala-Pro-Val-pNA (EPC No. FH237) as substrate" from page 84 of Elastin Products Company, Inc. Research Biochemicals Catalogue (2004, 92 pages).

Trypsin Inhibition

Trypsin is a proteolytic enzyme that is involved in in vivo epidermal proliferation and inflammation. Trypsin inhibition activity was determined by a kinetic colorimetric assay designed for use with 96-well microtiter plates (microplates) and computer-controlled microplate reader. Enzymatic activity in cleaving the substrate was indicated by a development of yellow color measured as increase in absorbance at 405 nm wavelength. The mean of maximum rates of absorbance increase for negative control wells was considered as 100% of enzyme activity, and IC50 was calculated as concentration of sample in the well necessary to reduce the enzyme activity to 50%. Lower IC50 values indicate higher trypsin inhibition activity. L-BAPA (Nα-Benzoyl-L-arginine 4-nitroanilide hydrochloride) substrate, trypsin, and solvent reagents were obtained from Sigma-Aldrich. pH 8.2 Tris-CaCl$_2$ buffer was used for preparing working solutions of trypsin and L-BAPA substrate. Deionized water was used as solvent for buffer reagents, as negative control, and as the diluents for preparing serial dilutions of the samples. Reaction volume in each well was 200 μA, with concentration of trypsin equal to 60 nM and substrate equal to 0.5 mM.

Antioxidant Activity

Antioxidant is an agent that reduces the damage caused by oxidation. Antioxidant activity was determined by ORAC testing using an adaptation of the method described in "Performing Oxygen Radical Absorbance Capacity (ORAC) Assays with Synergy HT Multi-Detection Microplate Reader" Application Note from BioTek available at (www.biotek.com/resources/docs/ORAC_Assay_Application_Note.pdf) for use with Synergy 2 microplate reader from BioTek Instruments Inc (Winooski, Vt.). In this assay, AAPH (2,2'-azobis 2-amino-propane) generates reactive oxygen species which damage the fluorescent probe (sodium fluorescein). Antioxidants such as (R)-Trolox methyl ether prevent or slow this damage, and their effects can be quantified by fluorescence measurements. Fluorescence readings were taken with excitation wavelength set at 485 nm and emission wavelength set at 528 nm, with reaction volume of 200 µA, AAPH concentration of 55 mM, sodium fluorescein concentration of 1.33 µM, and (R)-Trolox methyl ether concentration range between 80 µM and 2 µM. Sodium fluorescein (Fluka 46960), AAPH (Sigma 440914) and (R)-Trolox methyl ether (Fluka 93509) were obtained from Sigma-Aldrich (St. Louis, Mo.). AUC (Area Under Curve) values were calculated as sum of proportions (current fluorescence reading for the well divided by first fluorescence reading for the well). Average of AUC values of wells with deionized water was subtracted from AUC of wells with (R)-Trolox methyl ether and wells with test articles to obtain AUC corresponding to preservation of fluorescence by antioxidants. A calibration curve was generated as function of a wells' antioxidant-related AUC showing (R)-Trolox methyl ether weight-equivalent ORAC activity. ORAC activity for test articles was then calculated as units weight test article necessary to achieve antioxidant effect equal to one produced by 1 unit weight (R)-Trolox methyl ether, with lower numbers indicating higher ORAC activity.

DPPH (2,2-Diphenyl-1-Picrylhydrazyl) Free Radical Scavenging Activity

Free radical scavenger is an ingredient that reacts with free radicals in a biological system, reduces free radical-induced damage, and protects against the effects of free radicals. Free radical scavenging activity, i.e. DPPH (2,2-Diphenyl-1-Picrylhydrazyl) free radical scavenging activity, was determined by a kinetic colorimetric assay adapted for use with glass-coated polypropylene 96-well microtiter plates (catalog number 400 062) from SUN-SRi (Rockwood, Tenn.) and Synergy 2 microplate reader from BioTek Instruments Inc (Winooski, Vt.). Absorbance was measured at 515 nm wavelength. Reaction volume in each microplate well was 200 µl, with initial concentration of DPPH equal to 114 µM. L-ascorbic acid was used as positive control. DPPH (Sigma D9132) and USP L-ascorbic acid (Sigma A-2218) were obtained from Sigma-Aldrich (St. Louis, Mo.). Stoichiometry of the reaction was calculated and expressed as units weight test article necessary to quench 1 unit weight DPPH, with lower numbers indicating higher activity. This method was adapted from procedure described in "Use of a free radical method to evaluate antioxidant activity" by W. Brand-Williams et al, published in LWT—Food Science and Technology, Volume 28, Issue 1, 1995, pp 25-30.

Color

Gardner Scale

The Gardner Color scale as specified in ASTM D1544 is a single number colour scale for grading light transmitting samples with color characteristics ranging from light yellow to brownish red. The scale is defined by the chromaticities of glass standards numbered from 1 for the lightest to 18 for the darkest. The Gardner Color of samples was determined on the Lovibond Gardner Comparator 3000 (The Tintometer Limited of Salisbury, UK), a 3-field instrument for visually determining the Gardner Color of samples by direct comparison with colored glass standards.

Refractive Index, nD

Refractive Index was determined by measuring on Arias 500 refractometer from Reichert Analytical Instruments (Depew, N.Y.) with temperature regulation provided by Polystat model 12108-10 temperature controller from Cole-Parmer (Vernon Hills, Ill.). Procedure is based on the instruction manual for Arias 500 refractometer, sections 6.0, 4.1 and 4.4-4.5.

pH Determination pH is defined as minus the decimal logarithm of the hydrogen ion activity in a solution and used to determine acidity or basicity of a solution.

pH levels were determined on a pH meter Model 250 pH/ISE/conductivity meter from Denver Instrument Company (Bohemia, N.Y.) with pH/ATC electrode number 300729.1 (Denver Instrument Company). Procedure is based on Denver Instrument Company 301127.1 Rev. D manual, pages ii and 9-12.

Determination of Wavelength of Maximum Absorbance in UV Spectrum ($\lambda_{max}$, nm)

$\lambda_{max}$, nm was determined on Ultrospec 4300 pro UV/Visible spectrophotometer from Biochrom Ltd (Cambridge, UK), formerly under GE Healthcare, formerly known as Amersham Biosciences, with water heated cell holder (Amersham part # 80-2106-08). The procedure is based on sections 2 and 4 from Amersham manual number 80-2108-25 entitled SWIFT II Applications Software UV/Visible Spectrophotometers, and on pages 7 and 15 from Amersham manual number 80-2111-79 entitled Ultrospec 4300 pro UV/Visible Spectrophotometer User Manual. Instrument control was provided by SWIFT II software suite (Biochrom Ltd) and temperature regulation by CB20 Mini Circulator from Torrey Pines Scientific (Carlsbad, Calif.).

Determination of Protein

The Kjeldahl method was used to measure the protein nitrogen content

Microbiological Limits

Microbial content and limits: Total Plate Count, CFU/g; Mold and Yeast, CFU/g; E. coli; Salmonella sp.; Staphylococcus aureus; Pseudomonas sp. were determined according to US Pharmacopoeia XXX, NF25, <61>, Microbiological Limit Tests.

EXAMPLES

The following examples are intended to illustrate particular embodiments of the present invention, but are by no means intended to limit the scope of the present invention.

Example 1

Process for Preparing BAFSI of the Present Invention

In general, the process for preparing the bioactive compositions of the present invention is described in U.S. Pat. No. 7,442,391, which is incorporated by reference herein. Depending on the specific photosynthetic organism (plants, aquatic plants or algae) the regimes of this process can be further modified. Photosynthetic organisms are subjected to various stresses, harvested, collected, and washed to yield fresh biomass (plant or algae).

This fresh biomass is subjected to grinding, maceration, and pressing. Biomass is grinded at 3,000 rpm for 30 seconds. Grinded biomass is immediately pressed using a horizontal, continuous screw press (Compact Press "CP-6", Vincent Corporation, FL). The pressure on the cone is maintained at level 24 kg/cm$^2$, screw speed at 12 rpm, and the temperature increase is ≤5° C. As a result, cell juice is effectively separated from cell wall fraction. Cell juice is then filtered through nylon mesh to yield filtered plant cell juice.

Separation of fresh phytomass to cell wall fraction and cell intracellular juice is followed by fractionations of cell juice conducted to produce core BAFSI: membrane and serum fractions.

Filtered cell juice is exposed to microwave treatment in order to coagulate cell juice. The coagulated cell juice is cooled and then subjected to centrifugation or ultracentrifugation in order to yield membrane fraction and cell juice supernatant.

BAFSI membrane fraction is used to prepare skin care, sun care, hair care and personal care compositions containing BAFSI membrane fraction.

Cell juice supernatant "as is" can be considered as suitable BAFSI as well and used as bioactive ingredient.

In addition, cell juice supernatant can be used to prepare skin care, sun care, hair care and personal care compositions containing BAFSI.

Depending on the marine organisms or plant source, cell juice supernatant can be further subjected to refinement of cell serum to yield stable and active cosmetic ingredients. This is accomplished by removing from the cell serum the major components responsible for the irreversible transformations that lead to generation of unwanted precipitate and deterioration of color and odor. These procedures include, but are not limited to: pH adjustment, isoelectric precipitation, microwave treatment, heat treatment, cooling, centrifugation, vacuum filtration, and stabilization.

Isoelectric precipitation is used to yield a mixture containing cytoplasm fraction and cell serum fraction. Cell serum fraction is then subjected to microwave treatment to cause coagulation. In order to separate cell serum fraction from cytoplasm fraction, the mixture is subjected to centrifugation. Depending on the plant source, prior to microwave treatment, cell serum fraction can be pH-adjusted. After coagulation, the mixture is then cooled followed by filtration or centrifugation to yield cell serum filtrate. It should be noted that this procedure must be used immediately after separation of cell serum from cytoplasm fraction is completed. The quantitative criteria to evaluate the complete separation of cytoplasm fraction are the absence of detectable levels of high molecular weight proteins (e.g., absence of ribulose biphosphate carboxylase) in subsequent filtrate or supernatant. As an example, the precipitated cell juice supernatants may be separated in a refrigerated centrifuge for greater than or equal to 20 minutes at greater than or equal to 3,000 rpm, and an absence of the proteins having molecular weight of greater than or equal to 10,000 in cell serum achieved.

Cell serum filtrate is than stabilized with stabilizers, preservatives, chelating agents and antioxidants to yield cell serum-derived BAFSI.

Suitable preservatives for use in the present invention include, for example, potassium sorbate, sodium benzoate, sodium methyl paraben, and citric acid. Suitable stabilizers include, but are not limited to, pentylene glycol, ethylhexylglycerin, Suitable chelating agents include but are not limited to tetrasodium EDTA, disodium EDTA, oxalic acid, citric acid, tartaric acid. An example of a suitable antioxidant for use in the present invention is sodium metabisulfite.

BAFSI are captured and isolated via fresh plant fractionation technologies and are well suited for their utilization in skin care, sun care, hair care and personal care formulations and applications comprising at least one BAFSI and other cosmetically acceptable ingredients and actives.

The present invention also relates to a method for preparing the BAFSI-containing skin care, sun care, hair care and personal care compositions exhibiting optimal combination of the useful physico-chemical properties and biological activities that include, but are not limited to antioxidant and free radical scavenging activities; inhibition of enzymes associated with skin inflammation, skin ageing and environmental damage, skin protection and repair of human tissues.

Stabilized BAFSI demonstrate properties which fully satisfy all requirements of cosmetic ingredients. Stability studies indicate that cosmetic ingredients produced from cell serum via these methods are stable at room temperature for 12-24 months (i.e., they maintain physico-chemical integrity and activities).

Example 2

Preparation of BAFSI Serum Fractions from Giant Brown Kelp (*Macrocystis Pyrifera*)

*Macrocystis pyrifera* starts ranging in size from 15 cm to 60 cm in length were harvested off the Southern California Ocean floor. The starts were immediately bagged after collection with six to seven starts per bag in ocean water, packed in coolers with gel ice packs and shipped via overnight delivery to the laboratory in Ossining, N.Y. The kelp was placed in the aquariums within thirty minutes of delivery and left to acclimate in the circulating aquariums.

Four identical 150 liter aquariums were prepared prior to each shipment to replicate ocean conditions in the kelp's natural environment. Thirty-five (35) grams per liter of Coralife Scientific Grade artificial sea salt was mixed with deionized water and circulated through the aquariums. Twenty five milliliters of Part A and Part B Proline F/2 algae food was added to each aquarium.

The ranges of cultivation parameters used for control and stressed systems with Giant brown kelp (*Macrocystis pyrifera*) were: Control (No stress): Giant brown kelp (*Macrocystis pyrifera*) harvested from original cultivation conditions in deeper water and processed; Hydrostatic pressure stress only was on-going during all respective cultivation times; Cultivation times were: 72 hrs (3 days) or 96 hrs (4 days). Hydrostatic stress occurs when algae, which typically grow in deeper water (10 ft or deeper), for example, Giant brown kelp (*Macrocystis pyrifera*), are transferred and then cultivated in more shallow reservoirs (aquariums) with reduced hydrostatic pressure compared to the one existing in original cultivation conditions; Hydrostatic Stress+UVB Stress=2 mW/cm$^2$ UVB 3-12 hrs/day; Hydrostatic Stress+ Ozone Stress=100 mg/hr continuous injection; Hydrostatic Stress+Osmotic Stress–osmolality of cultivation media=75% of control.

Description of cultivation equipment and control system components and the ranges of cultivation parameters used in aquariums are described in Table 1 and Table 2, respectively.

Biomass samples of Giant brown kelp (*Macrocystis pyrifera*) were taken upon delivery and removed from the cultivation aquariums at specific cultivation times: 72 hrs (3 days), 96 hrs (4 days). After cutting off and discarding the holdfasts, the following parts of this macroalgae: blades, pneumatocysts and stipes were collected, rinsed and placed in receptacle of Grindomix GM 200 Knife Mill (Retsch, Germany) with stainless steel knife and gravity lid and grinded for 30 seconds at 3000 RPM.

The grinded biomass was then immediately pressed using a horizontal, continuous screw press (Compact Press "CP-6", Vincent Corporation, FL). The pressure on the cone was maintained at level 24 kg/cm$^2$, screw speed was at 12 rpm, and the temperature increase was ≤5° C. As a result, cell wall fraction was effectively separated from cell juice which was utilized for further fractionation.

Initial pH of cell juice was from 6.50 to 7.30. It was adjusted to pH about 4.0 and subjected to the microwave treatment at about 194 F (90° C.) for about 30 s., chilled to about 30 C, centrifuged and separated in a refrigerated centrifuge for greater than or equal to 45 minutes at greater than or equal 4,000 g.

The following composition of preservatives and stabilizers was used: potassium sorbate 0.1%; sodium benzoate 0.1%; sodium metabisulfite 0.1%, tetrasodium EDTA (Dissolvine 220S) 0.1% and pentylene glycol (Hydrolite 5) 1.9%.

Example 3

Product Specifications of BAFSI Serum Fractions from Giant Brown Kelp (*Macrocystis pyrifera*)

BAFSI from Giant brown kelp (*Macrocystis pyrifera*) was prepared according to the process described above in Example 2.

Analyses of BAFSI from Giant brown kelp (*Macrocystis pyrifera*) were conducted to determine their physico-chemical and microbial characteristics presented in Table 3.

TABLE 3

Physical, chemical and organolaeptic characteristics of BAFSI from Giant brown kelp (*Macrocystis pyrifera*)

| Characteristics | Description/Range |
|---|---|
| Appearance | Clear to Slightly Hazy Golden Yellow Liquid |
| Odor | Slight Characteristic |
| Solubility in water | Soluble in any ratio |
| Color (Gardner scale) | 1-3 |
| Dry matter (%) | 3.89-4.91 |
| Refractive index (nD) | 1.335-1.341 |
| pH | 3.7-4.2 |
| Absorbance (1:20 in DI Water) at 280 nm | 0.25-0.65 |
| Total Plate Count (CFU/gm) | <10 |
| Mold/Yeast (CFU/gm) | <10 |
| *E. coli* (CFU/gm) | Negative/10 gm |
| *Salmonella* sp. (CFU/gm) | Negative/10 gm |
| *Staphylococcus aureus* (CFU/gm) | Negative/10 gm |
| *Pseudomonas* sp. (CFU/gm) | Negative/10 gm |

BAFSI serum fractions from Giant brown kelp (*Macrocystis pyrifera*) were determined to be substantially protein-free (less than 0.027% determined by Kjeldahl method), stable (i.e., maintaining physical and chemical integrity) for at least 12-18 months while stored at a temperature of between 15 and 25° C. in closed containers protected from light. BAFSI from Giant brown kelp (*Macrocystis pyrifera*) is a biodegradable product.

Example 4

Modulatory Effects of Stress Factors on the Properties of BAFSI Serum Fractions from Giant Brown Kelp (*Macrocystis Pyrifera*)

BAFSI from Giant brown kelp (*Macrocystis pyrifera*) were analyzed to determine the impact of various stress factors on their physico-chemical properties (surface tension; surface modification properties; dry matter; osmolality) and biological activities using enzyme inhibition, antioxidant, and free-radical scavenging assays. The results are presented in FIGS. 3-10 and summarized in Table 4.

TABLE 4

*Macrocystis pyrifera* BAFSI, % difference from control (No stress)

| Stress Factors | Days Stressed | Dry Matter | Osmolality | Osmolality per percent dry weight content | Surface Tension | Water Contact Angle on Vitro Skin (decrease = hydrophilic modification) | DPPH Quenching (increase = lower efficacy) | Elastase Inhibition IC50 (decrease = higher efficacy) | Trypsin Inhibition IC50 (decrease = higher efficacy) |
|---|---|---|---|---|---|---|---|---|---|
| Control (No Stress) BASELINE | 0 | 0.00 | 0.00 | 0.00 | 0.00 | 0.00 | 0.00 | 0.00 | 0.00 |
| Hydrostatic stress only | 3 | 0.00 | 0.36 | 0.35 | −2.73 | Not Tested | Not Tested | −20.54 | −10.29 |
| | 4 | 0.00 | 1.78 | 1.79 | −4.26 | −2.00 | 15.94 | −50.20 | 13.00 |
| Hydrostatic Stress + UVB Stress 3 hrs/day | 3 | −13.85 | −10.30 | 4.14 | −2.92 | Not Tested | Not Tested | −8.85 | −3.27 |
| Hydrostatic Stress + UVB Stress 12 hrs/day | 4 | −18.94 | −10.21 | 10.78 | −4.34 | −21.00 | 536.86 | −46.52 | −16.94 |
| Hydrostatic Stress + Osmotic Stress | 4 | −22.20 | −20.87 | −20.70 | −0.59 | −2.90 | 34.80 | −47.85 | −8.20 |
| Hydrostatic Stress + Ozone Stress | 4 | −0.20 | −10.57 | 14.96 | −10.01 | −9.10 | 127.99 | −47.31 | 57.37 |

Figure 3:
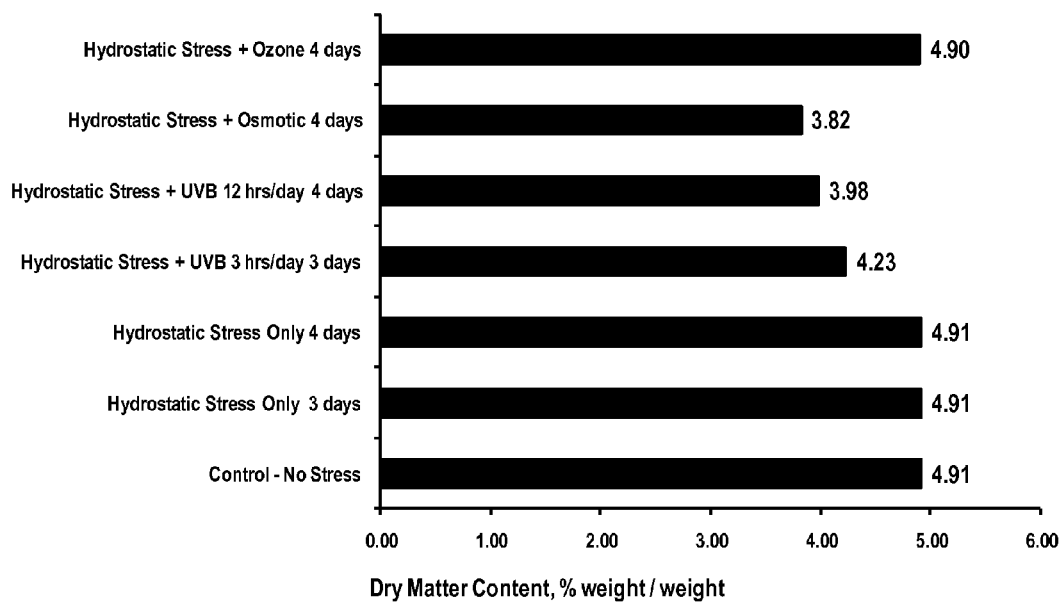
FIG. 3 is a graph showing the dry matter content (percent dry matter by weight) of various bioactive fractions of the present invention isolated from kelp.

Stresses have modulatory effects on the respective physico-chemical properties (surface tension; surface modification properties; dry matter; osmolality) of BAFSI from Kelp, as evidenced by the variation (e.g. decrease) in dry matter. Additionally, osmotic stress results in lowest dry matter content, which can be explained by mechanisms of coping with lower osmotic pressure (FIG. 3).

Figure 4:
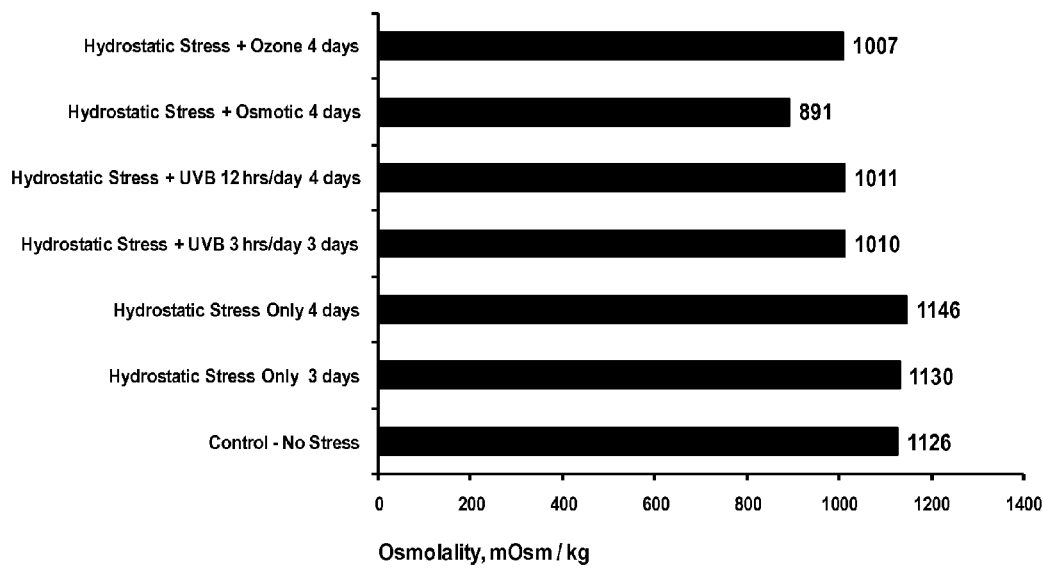
FIG. 4 is a graph showing the osmolality values of the various kelp samples of the present invention as milliOsmoles per kilogram (mOsm/kg).

Osmolality follows a somewhat similar pattern to dry matter (FIG. 4).

However, when comparing the number of particles generated by same amount of dry matter content, the differences are more telling, especially for osmotic stressed kelp.

Figure 5:
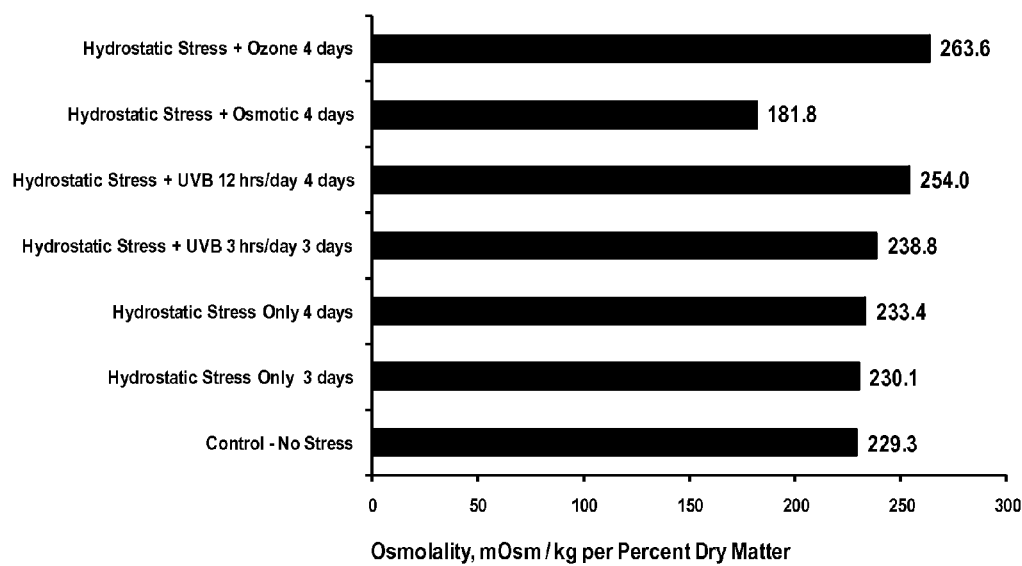
FIG. 5 is a graph showing the osmolality (mOsm/kg) produced per percent dry weight content of various kelp samples of the present invention.

It could be that kelp cell components have bound a greater number of particles, decreasing relative osmolality further, or that relatively small particles such as molecules and ions of lower molecular weight have been transported out of the cells (FIG. 5).

Figure 6:
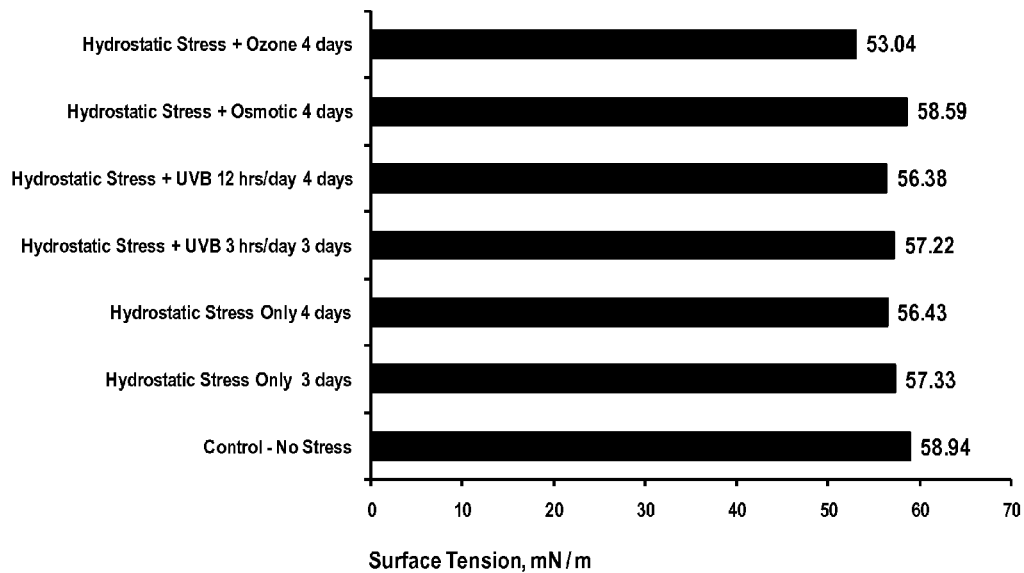
FIG. 6 is a graph showing the surface tension values of various kelp samples of the present invention, expressed as milliNewtons per meter (mN/m).

Surface tension depends on the concentration and nature of solutes and varies depending on the applied stress factor(s) and simultaneously helps to assess the composition changes due to stress factors (FIG. 6).

Figure 7:
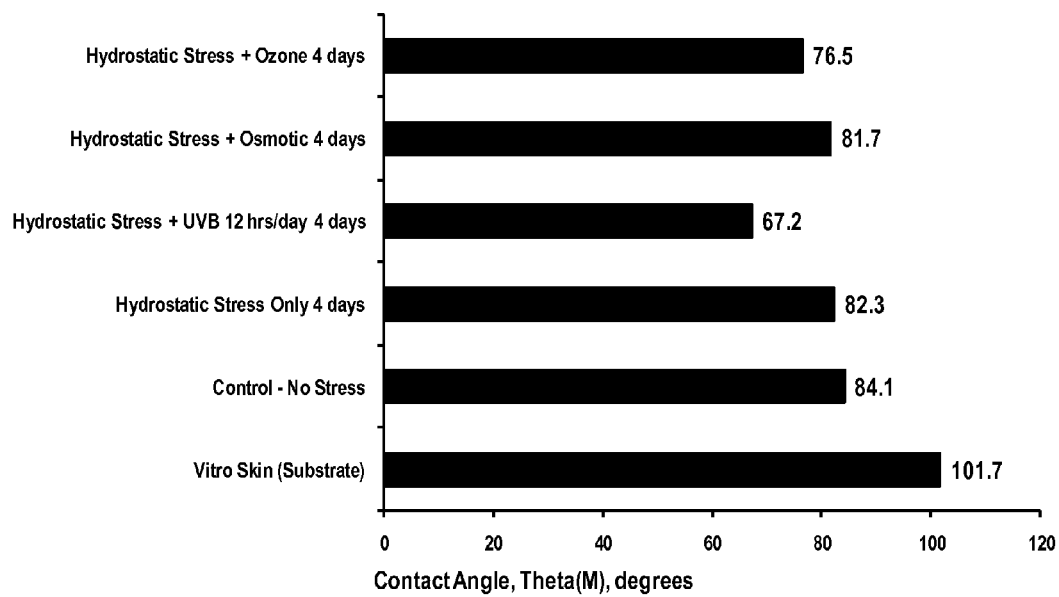
FIG. 7 is a graph showing the contact angle of deionized water on Vitro Skin substrate modified by various kelp samples of the present invention, expressed as degrees.

Stresses are capable of altering surface modification capabilities of resulting serum fractions. For example, if a hydrostatic stress is combined with certain UVB stress, BAFSI serum fractions capable of producing lower contact angles could be produced Skin care products produced with them could therefore have improved skin feel and moisturizing properties (FIG. 7).

Figure 8:
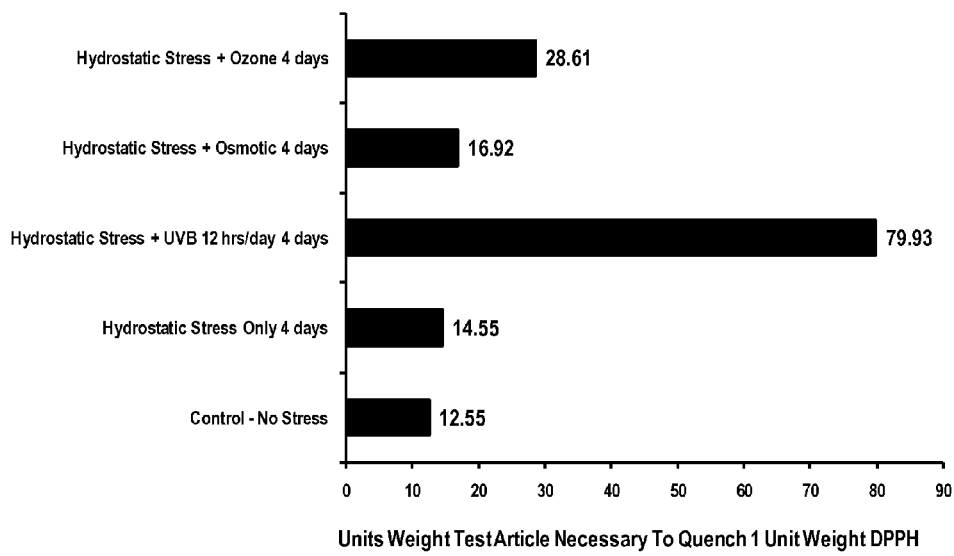
FIG. 8 is a graph showing the free radical quenching efficacy of various kelp samples of the present invention, expressed as units weight of the dry matter of the sample necessary to completely quench 1 unit weight DPPH. Lower values represent higher efficacy in quenching DPPH.

Free radical quenching measurements as measured by DPPH assay show that all stresses result in lower capacity; dramatically lower in case of hydrostatic stress combined with UVB stress. One possible reason would be that at given UVB exposure intensity and total duration much of the available and produced free radical quenching factors have been depleted (FIG. 8).

Figure 9:
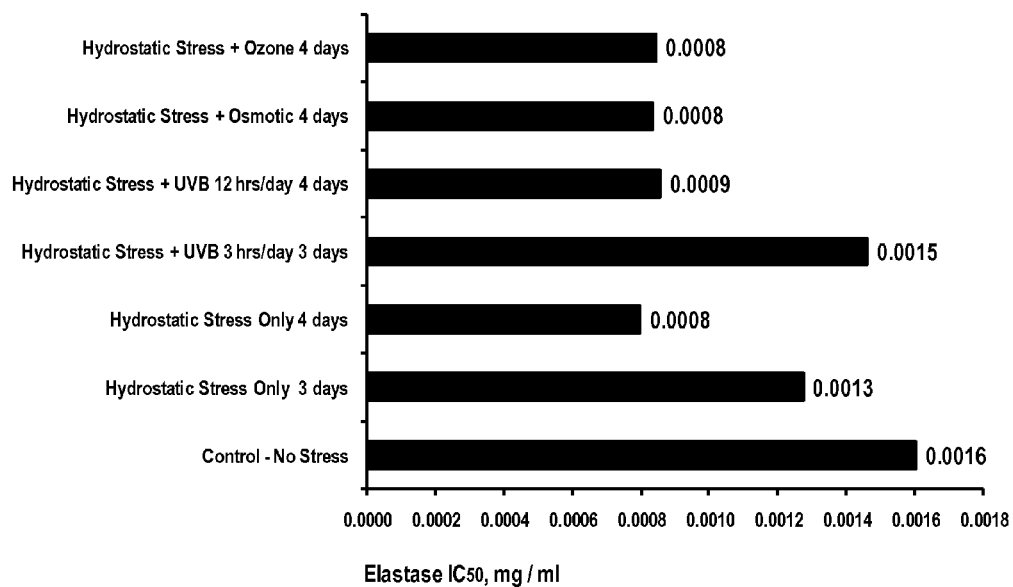
FIG. 9 is a graph showing the elastase $IC_{50}$ values shown as milligrams of dry matter of various kelp samples of the present invention per milliliter of reaction volume.

All stresses applied, hydrostatic stress alone and combined with osmotic, ozone and UV stresses improve the elastase-inhibiting activity, some very significantly (FIG. 9).

Figure 10:
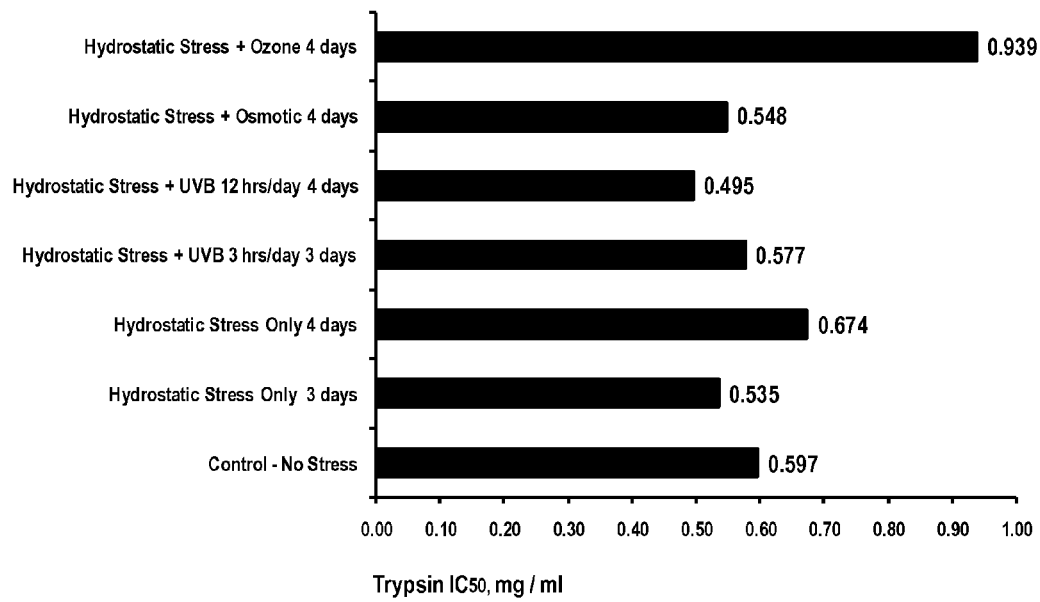
FIG. 10 is a graph showing the trypsin $IC_{50}$ values shown as milligrams of dry matter of various kelp samples of the present invention per milliliter of reaction volume.

Stresses can induce changes in more specific activities, such as increasing the trypsin-inhibiting activity in case of hydrostatic stress combined with certain UVB stress and reducing this activity under other stress factors (FIG. 10).

Increase of elastase and trypsin inhibition activity of selected BAFSI from Giant brown kelp (*Macrocystis pyrifera*) indicates an improvement of their anti-inflammatory and anti-ageing properties.

Example 5

Comparison of Elastase Inhibition by BAFSI Serum Fractions from Giant Brown Kelp (*Macrocystis pyrifera*) vs. Elastase Inhibition by Alginate It is known that alginates are capable of reducing elastase activity, leading to their use in applications such as wound dressings where anti-inflammatory properties are desirable (Influence of alginate and alginate containing silver on elastase and ROS activity in vitro, C. Wiegand et al, Annual Congress 2006 of the ETRS 13.09.-16.09.2006, Pisa/Italy).

Dry matter of kelp blades contains 17%-25% alginates by weight (Monthly Determination of Alginate, M/G Ratio, Mannitol, and Minerals in Cultivated *Laminaria japonica*, Masura Honya et al, Nippon Suisan Gakkaishi, 59(2), pp 295-299, 1993).

To check the contribution of alginate to elastase inhibitory activity of kelp BAFSI, a sample of sodium alginate (Alginic acid sodium salt, from brown algae, A2158) was obtained from Sigma-Aldrich (St. Louis, Mo.). A solution of sodium alginate in deionized water, 0.2% w/w was prepared by stirring and sonication. A series of dilutions of this solution was tested alongside series of dilutions of two different kelp BAFSI serum fractions according to method for determining elastase inhibition as defined earlier.

Elastase $IC_{50}$ of sodium alginate was determined to be 0.0075 mg/ml. In the same test, kelp BAFSI dry matter $IC_{50}$ was determined to be 0.0012 mg/ml for one serum fraction and 0.0009 mg/ml for another serum fraction. This also corresponds well with the values shown for kelp BAFSI elastase $IC_{50}$ in FIG. 9.

The demonstrated difference is significant even with the improbable assumption that kelp BAFSI serum fraction dry matter is composed of 100% alginate. If one takes into account the more likely level of alginate as mentioned above, the difference is dramatic.

Therefore, elastase inhibitory activity of kelp BAFSI serum fractions dry matter is greater than that of pure sodium alginate which can be explained by the contribution of other components more potent than alginate at inhibiting elastase.

Example 6

Thermal Stability of Elastase Inhibitory Activity of Selected BAFSI Serum Fractions from Giant Brown Kelp (*Macrocystis pyrifera*)

Thermal stability of elastase inhibitory activity of selected kelp BAFSI serum fraction was tested by taking three identical aliquots of the same serum fraction, storing them in identical containers at different temperatures for 6 days and determining their elastase inhibition activity according to the method described above.

Elastase $IC_{50}$ of the sample stored at 4° C. was 0.0012 mg/ml, $IC_{50}$ of the sample stored at 60° C. was 0.0012 mg/ml, and $IC_{50}$ of the sample stored at 80° C. was 0.0011 mg/ml.

Therefore, the elastase inhibitory activity of kelp BAFSI serum fractions can remain stable after exposure to elevated temperatures typically used in thermal stability and accelerated aging studies.

Example 7

Preparation of BAFSI Serum Fractions from Green Algae (*Chaetomorpha linum*)

Green algae (*Chaetomorpha linum*) are known for their fast growth rate, ability to survive at relatively high temperatures and demonstrate higher levels of photosynthetic activity when compared with giant kelp.

The Green algae was aqua cultured (Live Aquaria.com Aquaculture Coral & Marine Life Facility, CA.). It was harvested, bagged and shipped via overnight delivery to the laboratory in Ossining, N.Y. The Green Algae was removed from the shipping bags. One portion of Biomass was taken and processed for the Control Day 0 sample. The remainder of the Green Algae was proportioned and placed into the four aquariums all at water temperature of about 25.0 degrees C. within thirty minutes of delivery.

The ranges of cultivation parameters used for control and stressed systems with Green algae (*Chaetomorpha linum*) were: Control; UVB Stress=2 mW/cm$^2$ UVB 12 hrs/day; Ozone Stress=100 mg/hr continuous injection; Osmotic Stress–osmolality of cultivation media=85% of control; Cultivation time: 24 hrs (1 day), 96 hrs (4 days), 288 hrs (12 days), 456 hrs (19 days).

Description of cultivation equipment and control system components and the ranges of cultivation parameters used in aquariums are described in Table 1 and Table 2, respectively.

Biomass samples of Green algae (*Chaetomorpha linum*) were removed from cultivation aquariums at specific cultivation times: 0 hrs, 24 hrs (1 day), 96 hrs (4 days), 288 hrs (12 days), 456 hrs (19 days), rinsed and placed in receptacle of Grindomix GM 200 Knife Mill (Retsch, Germany) with stainless steel knife and gravity lid. The Green Algae was grinded for 30 seconds at 3000 rpm.

The Grinded Biomass was then immediately pressed using a horizontal, continuous screw press (Compact Press "CP-6", Vincent Corporation, FL). The pressure on the cone was maintained at level 24 kg/cm$^2$, screw speed was at 12 rpm, and the temperature increase was ≤5° C. As a result, cell wall fraction was effectively separated from cell juice which was utilized for further fractionation.

Initial pH of cell juice varied from 6.30 to 7.90.

It was adjusted to pH about 4.0 and subjected to the microwave treatment at about 194 F (90 C) for about 30 sec, chilled to about 30 C, centrifuged and separated in a refrigerated centrifuge for greater than or equal to 45 minutes at greater than or equal to 4000 g.

The following composition of preservatives and stabilizers was used: potassium sorbate 0.1%; sodium benzoate 0.1%; sodium metabisulfite 0.1%, tetrasodium EDTA (Dissolvine 220S) 0.1% and pentylene glycol (Hydrolite 5) 1.9%.

Example 8

Product Specifications of BAFSI Serum Fractions from Green Algae (*Chaetomorpha linum*)

BAFSI from green algae (*Chaetomorpha linum*) were prepared according to the process described above in Example 7. Analyses of BAFSI from Green algae (*Chaetomorpha linum*) were conducted to determine its physico-chemical and microbial characteristics.

Table 5 summarizes the physical and chemical and organolaeptic characteristics of BAFSI (serum fraction) from Green algae (*Chaetomorpha linum*).

TABLE 5

Physical, chemical and organolaeptic characteristics of BAFSI (serum fraction) from Green algae (*Chaetomorpha linum*)

| Characteristics | Description/Range |
|---|---|
| Appearance | Clear to Slightly Hazy Golden Yellow Liquid |
| Odor | Slight Characteristic |
| Solubility in water | Soluble in any ratio |
| Color (Gardner scale) | 1-3 |
| Dry matter (%) | 3.20-6.30 |
| pH | 3.7-4.2 |
| Total Plate Count (CFU/gm) | <10 |
| Mold/Yeast (CFU/gm) | <10 |
| *E. coli* (CFU/gm) | Negative/10 gm |
| *Salmonella* sp. (CFU/gm) | Negative/10 gm |
| *Staphylococcus aureus* (CFU/gm) | Negative/10 gm |
| *Pseudomonas* sp. (CFU/gm) | Negative/10 gm |

BAFSI from Green algae (*Chaetomorpha linum*) were determined to be stable (i.e., maintaining physical and chemical integrity) for at least 12-18 months while stored at a temperature of between 15 and 25° C. in a closed container protected from light. BAFSI from Green algae (*Chaetomorpha linum*) is a biodegradable product.

Example 9

Modulatory Effects of Stress Factors on the Properties of the BAFSI Serum Fractions from Green Algae (*Chaetomorpha linum*)

BAFSI from Green algae (*Chaetomorpha linum*) were analyzed to determine the impact of various stress factors on their physico-chemical properties (surface tension; dry matter; osmolality) and biological activities using enzyme inhibition and anti-oxidant assays. The relative differences from controls are presented in FIGS. 11-16 and summarized in Table 6.

TABLE 6

*Chaetomorpha linum* BAFSI, % difference from control for respective day

| Stress Factors | Days Stressed | Dry Matter | Osmolality | Osmolality per percent dry weight content | Surface Tension | Elastase IC50 (lower numbers = higher efficacy) | ORAC (lower numbers = higher efficacy) |
|---|---|---|---|---|---|---|---|
| UVB | 0 | 0.00 | 0.00 | 0.00 | 0.00 | 0.00 | 0.00 |
|  | 1 | 3.41 | −0.41 | −3.69 | −0.07 | 2.52 | −19.13 |
|  | 4 | 27.31 | 55.02 | 21.97 | 3.70 | −45.13 | 8.95 |
|  | 12 | −3.48 | 3.25 | 6.97 | 3.02 | −24.29 | −42.71 |
|  | 19 | 2.93 | 34.59 | 30.76 | 19.56 | −76.39 | −34.91 |
| Ozone | 0 | 0.00 | 0.00 | 0.00 | 0.00 | 0.00 | 0.00 |
|  | 1 | −1.91 | −8.68 | −6.90 | 7.55 | −30.33 | −0.86 |
|  | 4 | 25.24 | 32.66 | 5.92 | 8.12 | −38.29 | 11.12 |
|  | 12 | −6.98 | −9.25 | −2.44 | −5.62 | −20.99 | −9.12 |
|  | 19 | −8.04 | −7.67 | 0.40 | 0.08 | 1.18 | 0.25 |

TABLE 6-continued

Chaetomorpha linum BAFSI, % difference from control for respective day

| Stress Factors | Days Stressed | Dry Matter | Osmolality | Osmolality per percent dry weight content | Surface Tension | Elastase IC50 (lower numbers = higher efficacy) | ORAC (lower numbers = higher efficacy) |
|---|---|---|---|---|---|---|---|
| Osmotic | 0 | 0.00 | 0.00 | 0.00 | 0.00 | 0.00 | 0.00 |
|  | 1 | −1.41 | −2.90 | −1.51 | −0.88 | 8.64 | −3.72 |
|  | 4 | 52.63 | 57.05 | 2.90 | 9.56 | −34.55 | 45.17 |
|  | 12 | −40.33 | −43.66 | −5.59 | −1.03 | 117.38 | −3.84 |
|  | 19 | 30.05 | 30.96 | 0.70 | −0.40 | −60.24 | 14.80 |

Figure 11:
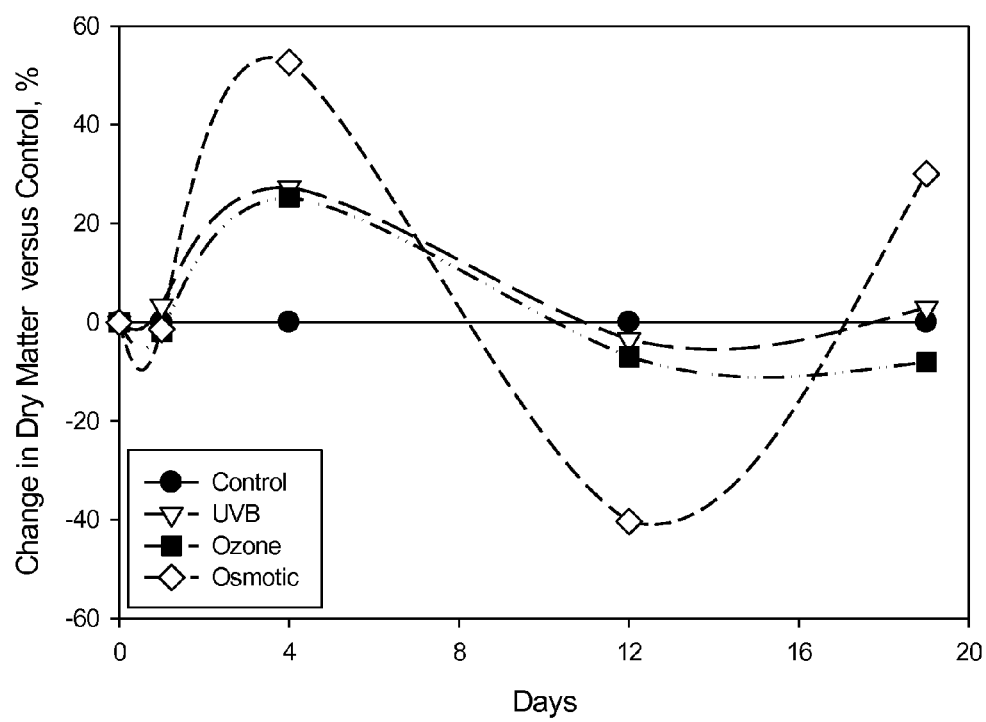
FIG. 11 is a graph showing the changes in dry matter content of BAFSI from *Chaetomorpha* versus control. The test articles are shown as percentage difference from the control sample taken on the same day.

As with macroalgae (kelp), stresses also modulate productivity (dry matter levels) of green algae. The changes in dry matter content of the test articles shown as percentage difference from the control sample taken on the same day are particularly dramatic for osmotic-stressed *Chaetomorpha linum* (FIG. 11).

Figure 12:
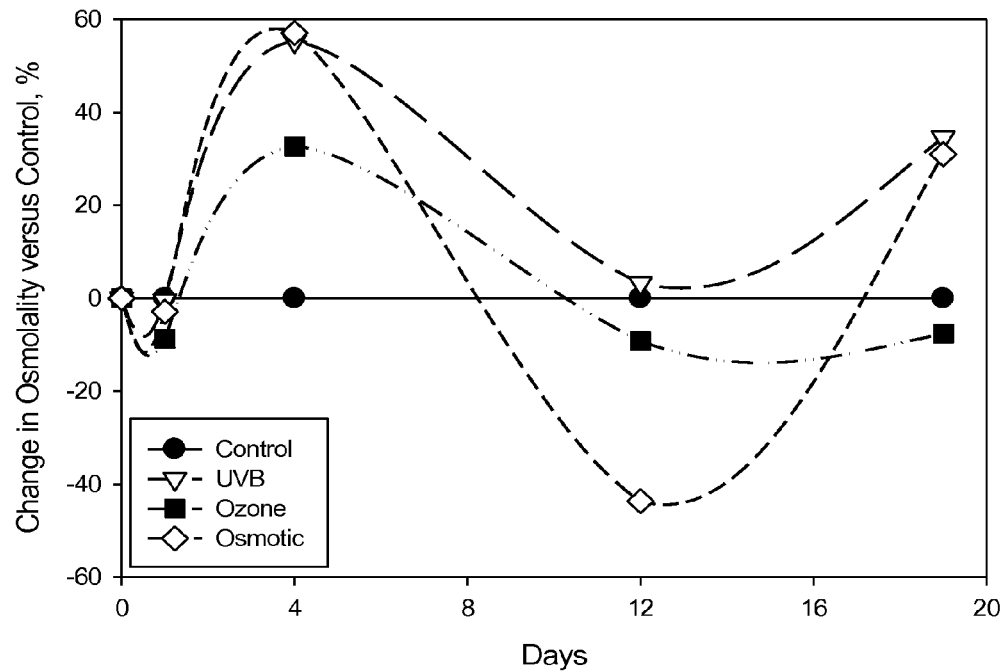
FIG. 12 is a graph showing the changes of osmolality of BAFSI from *Chaetomorpha* versus control. The test articles shown as percentage difference from control sample taken on the same day.
Figure 13:
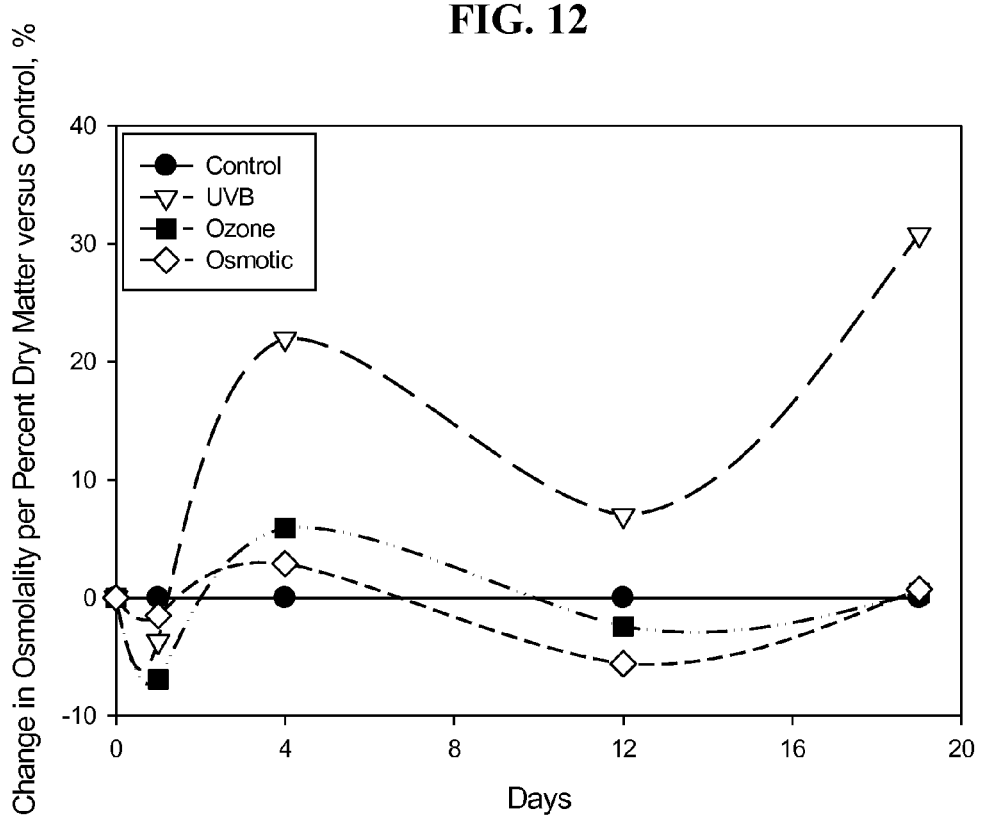
FIG. 13 is a graph showing the changes in osmolality per percent dry matter of BAFSI from *Chaetomorpha* versus control. The test articles are shown as percentage difference from control sample taken on the same day.

As with kelp, osmolality of BAFSI serum fractions from *Chaetomorpha linum* follows the similar pattern as dry matter content (FIG. 12). Unlike kelp, the number of particles generated by a given weight of BAFSI serum fractions from green algae dry matter does not fluctuate much with exception of UVB-stressed green algae. This may indicate a different mechanism for stress adaptation for green algae (*Chaetomorpha linum*) VS. macroalgae (*Macrocystis pyrifera*) (FIG. 13).

Figure 14:
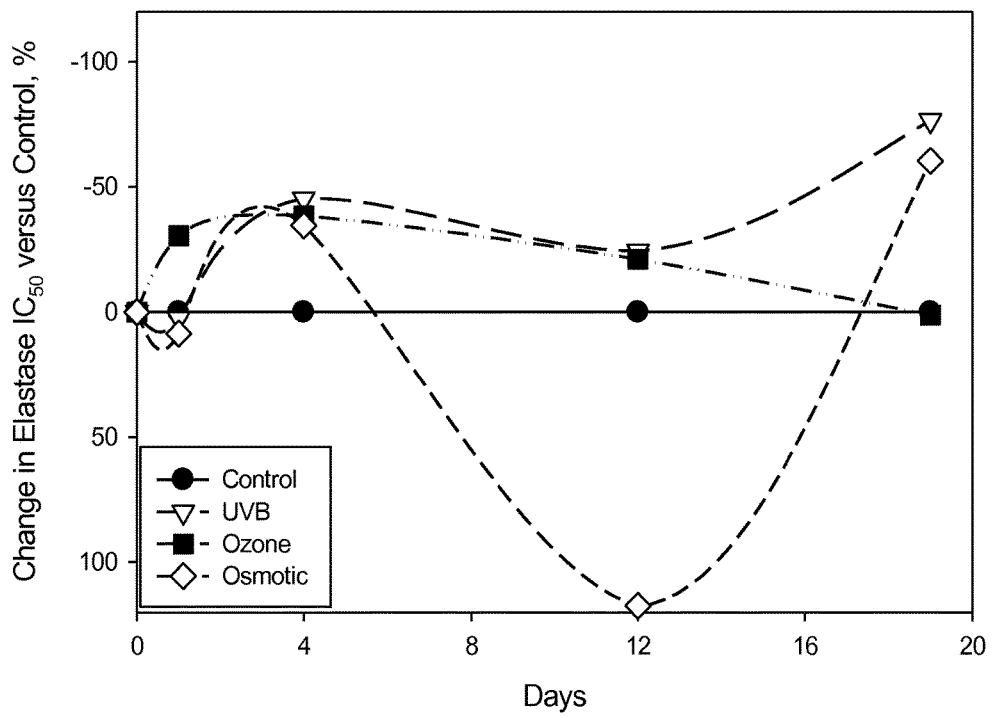
FIG. 14 is a graph showing the changes in elastase inhibition of BAFSI from *Chaetomorpha* versus control, shown as percentage difference from control sample taken on the same day. The protocol provides $IC_{50}$ results calculated for the dry matter of test articles. Lower $IC_{50}$ values represent higher inhibition and negative changes are shown as higher on this graph.

Brief stresses regardless of their nature increase the ability of serum fractions to inhibit elastase, especially for UVB and ozone-stressed *Chaetomorpha linum* (FIG. 14).

Figure 15:
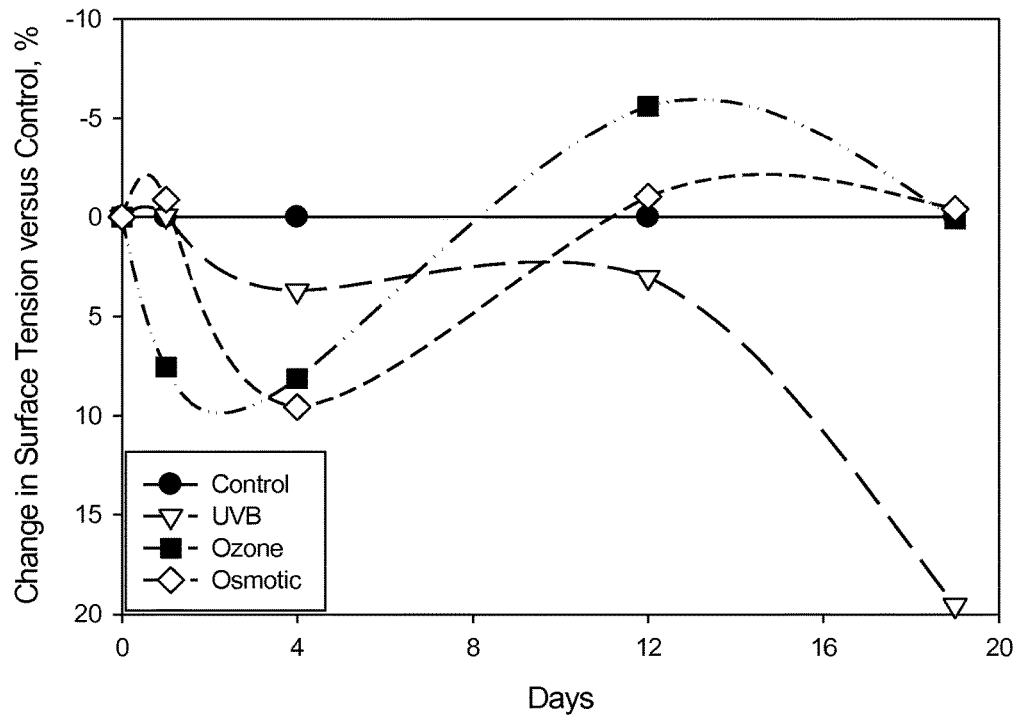
FIG. 15 is a graph showing the changes in surface tension of BAFSI from *Chaetomorpha* versus control, expressed as percentage difference from control sample taken on same day.

Stresses modulate surface tension of all BAFSI serum fractions from *Chaetomorpha linum*. Greater durations show significant divergence (FIG. 15)

Figure 16:
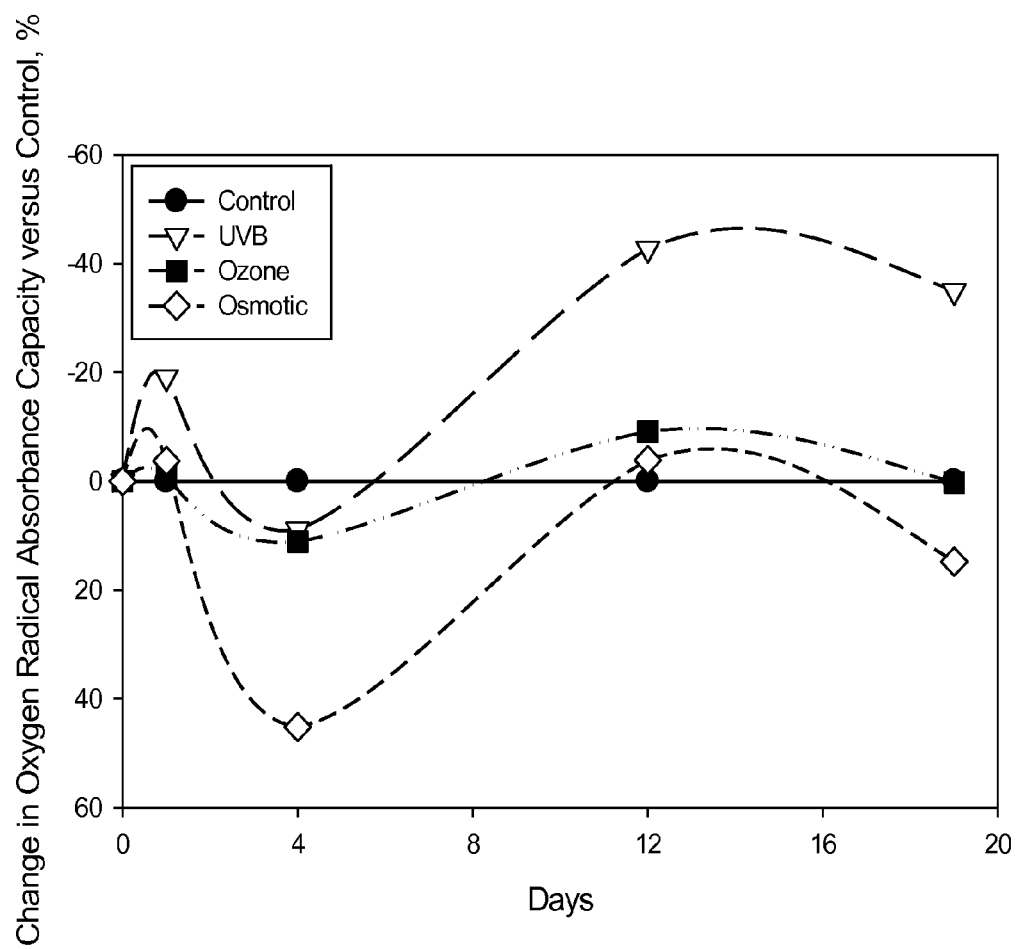
FIG. 16 is a graph showing the changes in oxygen radical absorbance capacity (ORAC) of BAFSI from *Chaetomorpha* versus control, expressed as percentage difference from control sample taken on the same day. The test protocol used provides results as inverse (R)-Trolox methyl ether weight equivalence (i.e., X units dry weight test article to achieve same antioxidant effect as 1 unit weight (R)-Trolox methyl ether). Therefore the lower numbers represent higher efficacy, and negative changes are shown as higher on this graph.

UVB stress increases the Oxygen Radical Absorbance Capacity of BAFSI serum fraction from *Chaetomorpha linum* (FIG. 16).

Example 10

Skin Lotion

| Trade Name | INCI-Name/Chemical-Name | Supplier | % w/w (as supplied) | | | |
|---|---|---|---|---|---|---|
| Part A | | | | | | |
| Arlacel 165 V | Glyceryl Stearate (and) PEG-100 Stearate | Uniqema | 1.80 | 1.80 | 1.80 | 1.80 |
| Tegosoft TN | C12-15 Alkyl Benzoate | Degussa | 5.00 | 5.00 | 5.00 | 5.00 |
| Dermofeel BGC | Butylene Glycol Dicaprylate/Dicaprate | Dr. Straetmans | 5.00 | 5.00 | 5.00 | 5.00 |
| Tegosoft P | Isopropyl Palmitate | Degussa | 2.00 | 2.00 | 2.00 | 2.00 |
| Lanette O | Cetearyl Alcohol | Cognis | 1.50 | 1.50 | 1.50 | 1.50 |
| Neo Heliopan 303 | Octocrylene | Symrise | 5.00 | 5.00 | 5.00 | 5.00 |
| Parsol 1789 | Butyl Methoxydibenzoylmethane* | DSM | 2.50 | 2.50 | 2.50 | 2.50 |
| TINOSORB ® S | Bis-Ethylhexyloxyphenol Methoxyphenyl Triazine* | BASF | 1.70 | 1.70 | 1.70 | 1.70 |
| Part B | | | | | | |
| Water | Water | | qs to 100% | qs to 100% | qs to 100% | qs to 100% |
| Propylene Glycol | Propylene Glycol | Rita Corporation | 2.00 | 2.00 | 2.00 | 2.00 |
|  | BAFSI Example 2 or 7** | IBT, LLC | 0.10 | 1.00 | 2.00 | 5.00 |
| Dissolvine NA-2-P | Disodium EDTA | Akzo Nobel | 0.20 | 0.20 | 0.20 | 0.20 |
| Amphisol K | Potassium Cetyl Phosphate | DSM | 2.50 | 2.50 | 2.50 | 2.50 |
| Part C | | | | | | |
| Eusolex 232 | Phenylbenzimidazole Sulfonic Acid* | Merck | 1.50 | 1.50 | 1.50 | 1.50 |
| Water | Water | | 3.75 | 3.75 | 3.75 | 3.75 |
| Tris Amino | Tromethamine | Angus | q.s. | q.s. | q.s. | q.s. |
| Part D | | | | | | |
| SALCARE ® SC91 | Sodium Acrylates Copolymer (and) Mineral Oil (and) PPG-1 Trideceth-6 | BASF | 1.00 | 1.00 | 1.00 | 1.00 |

-continued

| | Composition | | | | | |
|---|---|---|---|---|---|---|
| Trade Name | INCI-Name/Chemical-Name | Supplier | % w/w (as supplied) | | | |
| | Part E | | | | | |
| Dow Corning 345 Fluid | Cyclomethicone | Dow Corning | 3.00 | 3.00 | 3.00 | 3.00 |
| Preservative | | | qs | qs | qs | qs |

Manufacturing Instructions:

Heat up part A and part B (without Amphisol K) to 80° C., then add Amphisol K into part B and stir slowly during few minutes. Add part A into part B and mix well. Add part C. Cool down under continuous stirring and add part D by around 60° C. Afterwards add part F below 40° C. Alternatively, BAFSI can be post-added to the system after emulsion is formed. *Optional Sunscreen Actives. **Addition of BAFSI improves anti-ageing and other functional properties of the formulation.

Example 11

Sun Protective Gel

| | Composition | | | | | |
|---|---|---|---|---|---|---|
| Trade Name | INCI-Name/Chemical-Name | Supplier | % w/w (as supplied) | % w/w (as supplied) | % w/w (as supplied) | % w/w (as supplied) |
| | Part A | | | | | |
| Finsolv EB | Ethylhexyl Benzoate | Finetex | 5.00 | 5.00 | 5.00 | 5.00 |
| DUB VCI10 | Isodecyl Neopentanoate | Dubois Stearinerie | 5.00 | 3.00 | 3.00 | 3.00 |
| Neo Heliopan 303 | Octocrylene | Symrise | 2.50 | 2.50 | 2.50 | 2.50 |
| Neo Heliopan, Type OS | Ethylhexyl Salicylate | Symrise | 5.00 | 5.00 | 5.00 | 5.00 |
| Parsol 1789 | Butyl Methoxydibenzoylmethane | DSM | 3.00 | 3.00 | 3.00 | 3.00 |
| TINOSORB ® S | Bis-Ethylhexyloxyphenol Methoxyphenyl Triazine | BASF | 2.00 | 2.00 | 2.00 | 2.00 |
| | Part B | | | | | |
| Water | Water | | qs to 100% | qs to 100% | qs to 100% | qs to 100% |
| Glycerin 85% | Glycerin | Fluka | 3.00 | 3.00 | 3.00 | 3.00 |
| | BAFSI Example 2 or 7** | IBT, LLC | 0.10 | 1.00 | 2.00 | 4.00 |
| Keltrol RD | Xanthan Gum | Rahn | 0.20 | 0.20 | 0.20 | 0.20 |
| Dissolvine NA-2-P | Disodium EDTA | Akzo Nobel | 0.20 | 0.20 | 0.20 | 0.20 |
| TINOVIS ® GTC | Acrylates/Beheneth-25 Methylacrylate Copolymer | BASF | 2.50 | 2.50 | 2.50 | 2.50 |
| | Part C | | | | | |
| Sodium Hydroxide (30% solution) | Water (and) Sodium Hydroxide | Fluka | qs | qs | qs | qs |
| | Part D | | | | | |
| DOW CORNING ® 1503 FLUID | Dimethicone (and) Dimethiconol | Dow Corning | 2.00 | 2.00 | 2.00 | 2.00 |
| Orgasol 2002 D NAT COS 20 Microns | Nylon-12 | Atofina | 2.00 | 2.00 | 2.00 | 2.00 |
| | Preservative | | qs | qs | qs | qs |

Manufacturing Instructions:

Mix the ingredients of part B, disperse Xanthan Gum. Heat up part A and mix until homogeneous. Cool down to room temperature. Incorporate part A into part B with sufficient agitation. Neutralize with part C to pH 6-6.5. Finally add the ingredients of part D in the listed order. Alternatively, BAFSI can be post-added to the system after gel is formed. **Addition of BAFSI improves anti-ageing and other functional properties of the formulation.

Example 12

Moisturizing Lotion

| Trade Name | INCI-Name/ Chemical-Name | Supplier | % w/w (as supplied) | % w/w (as supplied) | % w/w (as supplied) | % w/w (as supplied) |
|---|---|---|---|---|---|---|
| Composition | | | | | | |
| Part A | | | | | | |
| Stearic Acid | Stearic Acid | J. T. Baker | 3.00 | 3.00 | 3.00 | 3.00 |
| Tegin M | Glyceryl Stearate | Evonik | 1.00 | 1.00 | 1.00 | 1.00 |
| Estol 3609 | Triethylhexanoin | Croda | 7.00 | 7.00 | 7.00 | 7.00 |
| Elefac I-205 | Octyldodecyl Neopentanoate | Bernel (Rovi) | 7.00 | 7.00 | 7.00 | 7.00 |
| Stantiv OMA-2 | Octadecene/MA Copolymer (and) various esters | Caschem | 1.00 | 1.00 | 1.00 | 1.00 |
| Finsolv EB | Ethylhexyl Benzoate | Finetex | 5.00 | 5.00 | 5.00 | 5..00 |
| Part B | | | | | | |
| Water | Water | | qs to 100% | qs to 100% | qs to 100% | qs to 100% |
| Glycerin | 85% Glycerin | Fluka | 5.00 | 5.00 | 5.00 | 5.00 |
| Dissolvine NA-2-P | Disodium EDTA | Akzo Nobel | 0.20 | 0.20 | 0.20 | 0.20 |
| | BAFSI Example 2 or 7** | IBT, LLC | 0.10 | 1.00 | 2.00 | 4.00 |
| Part C | | | | | | |
| VTEA 99% T | Triethanolamine | Dow Chemical | qs. | qs. | qs. | qs. |
| Part D | | | | | | |
| Dow Corning 200/350 cs Fluid | Dimethicone | Dow Corning | 1.00 | 1.00 | 1.00 | 1.00 |
| Part E | | | | | | |
| Mackaderm Asto-Dry | Aluminium Starch Octenylsuccinate | Mc Intyre | 5.00 | 5.00 | 5.00 | 5.00 |
| TINOVIS ® ADE | Sodium Acrylates Copolymer (and) Hydrogenated Polydecene (and) PPG-1 Trideceth-6 | BASF | 0.10 | 0.10 | 0.10 | 0.10 |

Manufacturing Instructions:

Heat up part A and part B to 80° C. Adjust pH of B to around 6, and then add A into B under high stirring speed. Cool down under stirring, adjust pH to 7. Add part D under stirring. Homogenize again by around 50° C. Below 40° C. add the ingredients of part E in the listed order. Adjust the final pH to around 7.0. Alternatively, BAFSI can be post-added to the system after it is formed. **Addition of BAFSI improves anti-ageing and other functional properties of the formulation.

Example 13

Sunscreen Lotion

| Trade Name | INCI-Name/ Chemical-Name | Supplier | % w/w (as supplied) | % w/w (as supplied) | % w/w (as supplied) | % w/w (as supplied) |
|---|---|---|---|---|---|---|
| | | Composition | | | | |
| | | Part A | | | | |
| Sensanov WR | C20-22 Alkyl Phosphate (and) C20-C22 Alcohols | Seppic | 4.00 | 4.00 | 4.00 | 4.00 |
| Cetiol B | Dibutyl Adipate | Cognis | 4.00 | 4.00 | 4.00 | 4.00 |
| Uvinul A Plus | Diethylamino Hydroxybenzoyl Hexyl Benzoate | BASF | 10.00 | 10.00 | 10.00 | 10.00 |
| Parsol MCX | Ethylhexyl Methoxycinnamate | DSM | 7.50 | 7.50 | 7.50 | 7.50 |
| TINOSORB ® S | Bis-Ethylhexyloxyphenol Methoxyphenyl Triazine | BASF | 2.00 | 2.00 | 2.00 | 2.00 |
| Uvinul T 150 | Ethylhexyl Triazone | BASF | 1.00 | 1.00 | 1.00 | 1.00 |
| | | Part B | | | | |
| Water | Water | | q.s.p 100% | q.s.p 100% | q.s.p 100% | q.s.p 100% |
| Dissolvine NA-2-P | Disodium EDTA | Akzo Nobel | 0.20 | 0.20 | 0.20 | 0.20 |
| | BAFSI Example 2 or 7** | IBT, LLC | 0.10 | 1.00 | 2.00 | 4.00 |
| Tris Amino Ultra Pur | Tromethamine | Angus Chemie GmbH | q.s. | q.s. | q.s. | q.s. |
| | | Part C | | | | |
| Dow Corning 246 Fluid | Cyclohexasiloxane (and) Cyclopentasiloxane | Dow Corning | 5.00 | 5.00 | 5.00 | 5.00 |
| | | Part D | | | | |
| TINOVIS ® ADE | Sodium Acrylates Copolymer (and) Hydrogenated Polydecene (and) PPG-1 Trideceth-6 | BASF | 0.40 | 0.40 | 0.40 | 0.40 |
| | | Part E | | | | |
| Preservative | | | q.s. | q.s. | q.s. | q.s. |

Manufacturing Instructions:

Heat up part A and part B to 75° C. with mixing until both are homogeneous. Add part A (75° C.) into part B (75° C.) and homogenize. At 60° C., add part C and mix until homogeneous. Add part D and homogenize. Cool down to room temperature, add part E and mix until homogeneous. Adjust pH to about 6.0. Alternatively, BAFSI can be post-added to the system after it is formed. **Addition of BAFSI improves anti-ageing and other functional properties of the formulation.

Example 14

Facial Gel Lotion

| Trade Name | INCI-Name/ Chemical-Name | Supplier | % w/w (as supplied) | | | |
|---|---|---|---|---|---|---|
| | | Composition | | | | |
| | | Part A | | | | |
| Tegosoft P | Isopropyl Palmitate | Evonik | 5.00 | 5.00 | 5.00 | 5.00 |
| Elefac I-205 | Octyldodecyl Neopentanoate | Bernel (Rovi) | 7.00 | 7.00 | 7.00 | 7.00 |

-continued

| Trade Name | INCI-Name/ Chemical-Name | Supplier | % w/w (as supplied) | | | |
|---|---|---|---|---|---|---|
| Part B | | | | | | |
| Water | Water | | qs to 100 | qs to 100 | qs to 100 | qs to 100 |
| Glycerin 85% | Glycerin | Fluka | 5.00 | 5.00 | 5.00 | 5.00 |
| Keltrol T | Xanthan Gum | Rahn | 0.20 | 0.20 | 0.20 | 0.20 |
| Dissolvine NA-2 | Disodium EDTA | Akzo Nobel | 0.10 | 0.10 | 0.10 | 0.10 |
| Part C | | | | | | |
| TINOVIS ® ADE | Sodium Acrylates Copolymer (and) Hydrogenated Polydecene (and) PPG-1 Trideceth-6 | BASF | 1.50 | 1.50 | 1.50 | 1.50 |
| Part D | | | | | | |
| | BAFSI Example 2 or 7** | IBT, LLC | 0.10 | 0.5 | 1.00 | 2.00 |
| Dry-Flo PC | Aluminum Starch Octenylsuccinate | Akzo Nobel | 1.00 | 1.00 | 1.00 | 1.00 |
| Preservatives | | | qs. | qs. | qs | qs. |

Manufacturing Instructions:

Add part A to part B under stirring. Homogenize for a short time. Add part C under stirring. When homogeneous add the ingredients of part D in the listed order. Alternatively, BAFSI can be post-added to the system after it is formed. **Addition of BAFSI improves anti-ageing and other functional properties of the formulation.

Example 15

Facial Toning Lotion

| Trade Name | INCI-Name/ Chemical-Name | Supplier | % w/w (as supplied) | | | |
|---|---|---|---|---|---|---|
| Part A | | | | | | |
| Water | Water | | qs to 100 | qs to 100 | qs to 100 | qs to 100 |
| Carbopol 940 (2% solution) | Carbomer | Lubrizol | 20.00 | 20.00 | 20.00 | 20.00 |
| Dissolvine 220S | Disodium EDTA | Akzo Nobel | 0.05 | 0.05 | 0.05 | 0.05 |
| Flexan II Polymer | Sodium Polystyrene Sulfonate | Akzo Nobel Surface Chemistry | 1.00 | 1.00 | 1.00 | 1.00 |
| Glycerin 85% | Glycerin | Fluka | 3.00 | 3.00 | 3.00 | 3.00 |
| Part B | | | | | | |
| Lanette O | Cetearyl Alcohol | BASF | 2.00 | 2.00 | 2.00 | 2.00 |
| Emerest 2400 | Glyceryl Monosarate | BASF | 1.00 | 1.00 | 1.00 | 1.00 |
| DC 245 | Cyclomethicone | Dow Corning | 1.50 | 1.50 | 1.50 | 1.50 |
| Crodamol GTCC | Caprylic/Capryc Triglycerides | Croda | 2.50 | 2.50 | 2.50 | 2.50 |
| Brij 721 | Steareth-21 | Croda | 0.80 | 0.80 | 0.80 | 0.80 |
| Brij 72 | Steareth-2 | Croda | 0.50 | 0.50 | 0.50 | 0.50 |
| Part C | | | | | | |
| | BAFSI Example 2 or 7** | IBT, LLC | 0.10 | 0.50 | 1.00 | 3.00 |
| Part D | | | | | | |
| Triethanolamine 99% | Triethanolamine | | qs. | qs. | qs | qs. |
| Preservatives | | | qs. | qs. | qs | qs. |

Manufacturing Instructions:

Separately combine Phase A and Phase B, and heat both to 80° C. Add Phase B to Phase B with high shear for 5 min. Mix for 15-30 min with moderate to low agitation. Cool to 40° C., add Phase C. If necessary, adjust pH to 5.8-6.3 and add preservatives (Phase D). Alternatively, BAFSI can be post-added to the system after it is formed. **Addition of BAFSI improves anti-ageing and other functional properties of the formulation.

Example 16

Anti-Ageing Serum

| Trade Name | INCI-Name/ Chemical-Name | Supplier | % w/w (as supplied) | | | |
|---|---|---|---|---|---|---|
| Composition | | | | | | |
| Part A | | | | | | |
| Water | Water | | qs to 100 | qs to 100 | qs to 100 | qs to 100 |
| Dissolvine 220-S | Tetrasodium EDTA | Akzo Nobel | 0.10 | 0.10 | 0.10 | 0.10 |
| Hydrolite 5 | Pentylene Glycol | Symrize | 1.50 | 1.50 | 1.50 | 1.50 |
| Glycerin 85% | Glycerin | Fluka | 3.00 | 3.00 | 3.00 | 3.00 |
| | BAFSI Example 2 or 7** | IBT, LLC | 0.01 | 10.00 | 50.00 | 95.00 |
| Part B | | | | | | |
| pH adjustors | | | qs. | qs. | qs | qs. |
| Preservatives | | | qs. | qs. | qs | qs. |

Manufacturing Instructions:

Combine Phase A one by one with sufficient agitation. Mix for 15-30 min with moderate to low agitation. If necessary, adjust pH to target level that depends on the target area, face (pH 4.0-6.9) or around-the-eye area (6.7-7.3) and add preservatives from Phase B. **Addition of BAFSI provides anti-ageing and other functional properties of the formulation.

Examples 10-16 above are non-limiting examples of the finished formulations of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

Citation of a reference herein shall not be construed as an admission that such reference is prior art to the present invention. All references cited herein are hereby incorporated by reference in their entirety.

What is claimed is:

1. A method for obtaining a bioactive fraction from a photosynthetic organism, said method comprising:
   providing an aquatic photosynthetic organism selected from the group consisting of Macrocystis spp. and Chaetomorpha spp.;
   cultivating the aquatic photosynthetic organism under stress-inducing cultivation conditions comprising subjecting the aquatic photosynthetic organism to a stress factor or to a plurality of stress factors;
   separating the stress-induced aquatic photosynthetic organism into cell juice and a cell walls component;
   treating the cell juice under conditions effective to yield a bioactive fraction, wherein said bioactive fraction is selected from the group consisting of a cell serum fraction, a membrane fraction, a cell juice supernatant fraction, and a cell serum filtrate fraction; and
   isolating said bioactive fraction from the treated cell juice,
   wherein the stress factor or plurality of stress factors are selected from the group consisting of ultraviolet light stress by applying UVB irradiance of 1-2 mW/cm$^2$ during 3-12 hours a day, ozone stress by injecting ozone to obtain a redox potential from 200 to 400 and a concentration of dissolved $O_2$ from 7.0 to 9.0 mg/l, osmotic pressure stress by applying osmolality of cultivation media from 600 to 1200 mOs/kg, reducing hydrostatic pressure compared to that in original conditions, and a combination thereof, and
   wherein the isolated bioactive fraction has at least one altered characteristic compared to a corresponding bioactive fraction isolated from a non-stress-induced aquatic photosynthetic organism, and
   said characteristic is selected from the group consisting of physico-chemical properties, surface modification properties, moisturization properties, anti-inflammatory activity, and anti-ageing activity,
   wherein the physico-chemical properties are properties selected from the group consisting of surface tension, dry matter content, and osmolality, and
   wherein the anti-inflammatory and/or anti-ageing activities are selected from the group consisting of elastase inhibition, trypsin inhibition, anti-oxidant activity, and free-radical scavenging activity.

2. The method according to claim 1, wherein said *Macrocystis* spp. is selected from the group consisting of *Macrocystis angustifolia, Macrocystis integrifolia, Macrocystis laevis*, and *Macrocystis pyrifera*.

3. The method according to claim 1, wherein said *Chaetomorpha* spp. includes, a *Chaetomorpha* spp. selected from the group consisting of *Chaetomorpha aerea, Chaetomorpha antennina, Chaetomorpha basiretorsa, Chaetomorpha brachygona, Chaetomorpha californica, Chaetomorpha cannabina, Chaetomorpha crassa, Chaetomorpha gracilis, Chaetomorpha linum, Chaetomorpha melagonium, Chaetomorpha natalensis*, and *Chaetomorpha spiralis*.

4. The method according to claim 1, wherein the bioactive fraction is a cell serum fraction.

5. The method according to claim 1, wherein the bioactive fraction is a membrane fraction.

6. The method according to claim 1, wherein the bioactive fraction is a cell juice supernatant fraction.

7. The method according to claim 1, wherein the bioactive fraction is a cell serum filtrate fraction.

8. A method for obtaining a bioactive fraction from a photosynthetic organism, said method comprising:
providing an aquatic photosynthetic organism selected from the group consisting of *Macrocystis* spp. and *Chaetomorpha* spp.;
cultivating the aquatic photosynthetic organism under stress-inducing cultivation conditions comprising subjecting the aquatic photosynthetic organism to a plurality of stress factors;
separating the stress-induced aquatic photosynthetic organism into cell juice and a cell walls component;
treating the cell juice under conditions effective to yield a bioactive fraction, wherein said bioactive fraction is selected from the group consisting of a cell serum fraction, a membrane fraction, a cell juice supernatant fraction, and a cell serum filtrate fraction; and
isolating said bioactive fraction from the treated cell juice,
wherein the plurality of stress factors include at least two stress factors selected from the group consisting of ultraviolet light stress by applying UVB irradiance of 1-2 mW/cm$^2$ during 3-12 hours a day, ozone stress by injecting ozone to obtain a redox potential from 200 to 400 and a concentration of dissolved $O_2$ from 7.0 to 9.0 mg/l, osmotic pressure stress by applying osmolality of cultivation media from 600 to 1200 mOs/kg, reducing hydrostatic pressure compared to that in original conditions, and a combination thereof, and
wherein the isolated bioactive fraction has at least one altered characteristic compared to a corresponding bioactive fraction isolated from a non-stress-induced aquatic photosynthetic organism, and
said at least one characteristic is selected from the group consisting of physico-chemical properties, surface modification properties, moisturization properties, anti-inflammatory activity, and anti-ageing activity,
wherein the physico-chemical properties are properties selected from the group consisting of surface tension, dry matter content, and osmolality, and
wherein the anti-inflammatory and/or anti-ageing activities are selected from the group consisting of elastase inhibition, trypsin inhibition, anti-oxidant activity, and free-radical scavenging activity.

9. The method according to claim 8, wherein said *Macrocystis* spp. includes a *Macrocystis* spp. selected from the group consisting of *Macrocystis angustifolia, Macrocystis integrifolia, Macrocystis laevis*, and *Macrocystis pyrifera*.

10. The method according to claim 8, wherein said *Chaetomorpha* spp. includes, a *Chaetomorpha* spp. selected from the group consisting of *Chaetomorpha aerea, Chaetomorpha antennina, Chaetomorpha basiretorsa, Chaetomorpha brachygona, Chaetomorpha californica, Chaetomorpha cannabina, Chaetomorpha crassa, Chaetomorpha gracilis, Chaetomorpha linum, Chaetomorpha melagonium, Chaetomorpha natalensis*, and *Chaetomorpha spiralis*.

11. The method according to claim 8, wherein the bioactive fraction is a cell serum fraction.

12. The method according to claim 8, wherein the bioactive fraction is a membrane fraction.

13. The method according to claim 8, wherein the bioactive fraction is a cell juice supernatant fraction.

14. The method according to claim 8, wherein the bioactive fraction is a cell serum filtrate fraction.

* * * * *